US009155639B2

(12) United States Patent  
Richter

(10) Patent No.: US 9,155,639 B2  
(45) Date of Patent: Oct. 13, 2015

(54) HELICAL HYBRID STENT

(75) Inventor: Jacob Richter, Arsuf (IL)

(73) Assignee: Medinol Ltd., Tel Aviv (IL)

( * ) Notice: Subject to any disclaimer, the term of this patent is extended or adjusted under 35 U.S.C. 154(b) by 110 days.

(21) Appl. No.: 12/764,418

(22) Filed: Apr. 21, 2010

(65) Prior Publication Data

US 2010/0274350 A1  Oct. 28, 2010

Related U.S. Application Data

(63) Continuation-in-part of application No. 12/428,347, filed on Apr. 22, 2009, now Pat. No. 8,382,821.

(51) Int. Cl.
*A61F 2/88* (2006.01)
*A61L 31/02* (2006.01)
(Continued)

(52) U.S. Cl.
CPC ............ *A61F 2/88* (2013.01); *A61L 31/022* (2013.01); *A61L 31/16* (2013.01); *A61F 2/91* (2013.01); *A61F 2220/005* (2013.01); *A61F 2220/0058* (2013.01); *A61F 2250/0068* (2013.01)

(58) Field of Classification Search
CPC .. A61F 2002/91558; A61F 2/88; A61F 2/885
USPC ............................................... 623/1.22, 1.42
See application file for complete search history.

(56) References Cited

U.S. PATENT DOCUMENTS 3,986,867 A  10/1976  Masumoto et al.
4,017,911 A  4/1977  Kafesjian et al.

(Continued)

FOREIGN PATENT DOCUMENTS

| AU | 2002 352871 | 9/2003 |
|---|---|---|
| AU | 2003-261912 | 3/2004 |

(Continued)

OTHER PUBLICATIONS

Office action and response of related U.S. Appl. No. 12/243,723 now U.S. Pat. No. 7,887,584. Supplemental Notice of Allowability dated Nov. 24, 2010; Supplemental Notice of Allowability dated Oct. 29, 2010; and Notice of Allowance and fees due dated Oct. 5, 2010.

(Continued)

*Primary Examiner* — Thomas J Sweet
*Assistant Examiner* — Seema Mathew
(74) *Attorney, Agent, or Firm* — Cadwalader Wickersham & Taft LLP

(57) ABSTRACT

An expandable helical stent is provided, wherein the stent may be formed of a main stent component and a securement. The main stent component is formed from a flat strip having one or more undulating side bands that may be connected to form geometrically shaped cells and are helically wound to form a stent. The helical coils of the main stent component may be spaced apart or nestled to each other. The nestling of the undulation of adjacent helical windings contributes to maintaining the tubular shape and uniformity of the helically coiled stent. Alternatively, the flat strip may comprise a single undulating pattern. At the ends of the main stent component are end bands, which when wound, form a cylindrical ring. In one embodiment, one or more struts of the main stent component may have a width sufficient to include one or more fenestrations. The fenestrated struts may be connected by loops or turns wherein the material is narrower than that of the fenestrated struts to provide enhanced flexibility. The helical tubular is maintained with a securement.

66 Claims, 9 Drawing Sheets

(51) Int. Cl.
  *A61L 31/16*   (2006.01)
  *A61F 2/91*    (2013.01)

(56) References Cited

U.S. PATENT DOCUMENTS

| | | | |
|---|---|---|---|
| 4,142,571 A | 3/1979 | Narasimhan | |
| 4,144,058 A | 3/1979 | Chen et al. | |
| 4,185,383 A | 1/1980 | Heimke et al. | |
| 4,281,706 A | 8/1981 | Liebermann et al. | |
| 4,409,041 A | 10/1983 | Datta et al. | |
| 4,440,585 A | 4/1984 | Kanehira | |
| 4,473,401 A | 9/1984 | Masumoto et al. | |
| 4,481,001 A | 11/1984 | Graham et al. | |
| 4,489,773 A | 12/1984 | Miller | |
| 4,614,221 A | 9/1986 | Masumoto | |
| 4,655,771 A | 4/1987 | Wallsten | |
| 4,733,665 A | 3/1988 | Palmaz | |
| 4,755,593 A | 7/1988 | Lauren | |
| 4,760,849 A | 8/1988 | Kropf | |
| 4,762,128 A | 8/1988 | Rosenbluth | |
| 4,800,882 A | 1/1989 | Gianturco | |
| 4,802,776 A | 2/1989 | Miyazawa et al. | |
| 4,856,516 A | 8/1989 | Hillstead | |
| 4,886,062 A | 12/1989 | Wiktor | |
| 4,969,458 A | 11/1990 | Wiktor | |
| 5,019,090 A | 5/1991 | Pinchuk | |
| 5,037,377 A | 8/1991 | Alonso | |
| 5,045,637 A | 9/1991 | Sato et al. | |
| 5,102,417 A | 4/1992 | Palmaz | |
| 5,104,404 A | 4/1992 | Wolff | |
| 5,116,360 A | 5/1992 | Pinchuk et al. | |
| 5,116,365 A | 5/1992 | Hillstead | |
| 5,122,154 A | 6/1992 | Rhodes | |
| 5,123,917 A | 6/1992 | Lee | |
| 5,128,214 A | 7/1992 | Takayanagi et al. | |
| 5,133,732 A * | 7/1992 | Wiktor | 623/1.22 |
| 5,135,536 A | 8/1992 | Hillstead | |
| 5,161,547 A | 11/1992 | Tower | |
| 5,195,984 A | 3/1993 | Schatz | |
| 5,282,824 A | 2/1994 | Gianturco | |
| 5,292,331 A | 3/1994 | Boneau | |
| 5,314,472 A * | 5/1994 | Fontaine | 623/1.22 |
| 5,368,659 A | 11/1994 | Peker et al. | |
| 5,370,683 A | 12/1994 | Fontaine | |
| 5,381,856 A | 1/1995 | Fujikura et al. | |
| 5,383,892 A | 1/1995 | Cardon et al. | |
| 5,393,594 A | 2/1995 | Koyfman et al. | |
| 5,405,377 A | 4/1995 | Cragg | |
| 5,421,919 A | 6/1995 | Roman | |
| 5,443,496 A | 8/1995 | Schwartz et al. | |
| 5,449,373 A | 9/1995 | Pinchasik et al. | |
| 5,464,438 A | 11/1995 | Menaker | |
| 5,510,077 A | 4/1996 | Dinh et al. | |
| 5,514,176 A | 5/1996 | Bosley | |
| 5,527,337 A | 6/1996 | Stack et al. | |
| 5,549,663 A | 8/1996 | Cottone et al. | |
| 5,554,181 A | 9/1996 | Das | |
| 5,554,182 A | 9/1996 | Dinh et al. | |
| 5,556,413 A | 9/1996 | Lam | |
| 5,562,729 A | 10/1996 | Purdy et al. | |
| 5,571,166 A | 11/1996 | Dinh et al. | |
| 5,575,818 A | 11/1996 | Pinchuk | |
| 5,591,197 A | 1/1997 | Orth et al. | |
| 5,591,198 A * | 1/1997 | Boyle et al. | 623/1.22 |
| 5,591,223 A | 1/1997 | Lock et al. | |
| 5,591,224 A | 1/1997 | Schwartz et al. | |
| 5,595,571 A | 1/1997 | Jaffe et al. | |
| 5,603,721 A | 2/1997 | Lau et al. | |
| 5,609,627 A | 3/1997 | Goicoechea et al. | |
| 5,618,299 A | 4/1997 | Khosravi et al. | |
| 5,626,604 A | 5/1997 | Cottone | |
| 5,628,785 A | 5/1997 | Scwartz et al. | |
| 5,632,771 A | 5/1997 | Boatman et al. | |
| 5,636,641 A | 6/1997 | Fariabi | |
| 5,653,747 A | 8/1997 | Dereume | |
| 5,672,169 A | 9/1997 | Verbeek | |
| 5,674,278 A | 10/1997 | Boneau | |
| 5,693,084 A | 12/1997 | Chuter et al. | |
| 5,693,085 A | 12/1997 | Buirge et al. | |
| 5,696,207 A | 12/1997 | Vargo et al. | |
| 5,716,396 A | 2/1998 | Williams, Jr. | |
| 5,720,776 A | 2/1998 | Chuter et al. | |
| 5,720,777 A | 2/1998 | Jaffe et al. | |
| 5,723,003 A | 3/1998 | Winston et al. | |
| 5,725,573 A | 3/1998 | Dearnaley et al. | |
| 5,728,150 A | 3/1998 | McDonald et al. | |
| 5,733,303 A | 3/1998 | Israel et al. | |
| 5,755,781 A | 5/1998 | Jayaraman | |
| 5,769,884 A | 6/1998 | Solovay | |
| 5,779,732 A | 7/1998 | Amundson | |
| 5,782,905 A | 7/1998 | Richter | |
| 5,788,626 A | 8/1998 | Thompson | |
| 5,797,443 A | 8/1998 | Lin et al. | |
| 5,800,456 A * | 9/1998 | Maeda et al. | 623/1.15 |
| 5,800,507 A | 9/1998 | Scwartz | |
| 5,800,508 A | 9/1998 | Goicoechea et al. | |
| 5,800,509 A | 9/1998 | Boneau | |
| 5,807,404 A | 9/1998 | Richter | |
| 5,810,872 A | 9/1998 | Kanesaka et al. | |
| 5,817,152 A | 10/1998 | Birdsall et al. | |
| 5,824,046 A | 10/1998 | Smith et al. | |
| 5,824,052 A | 10/1998 | Khosravi et al. | |
| 5,836,964 A | 11/1998 | Richter et al. | |
| 5,836,966 A | 11/1998 | St. Germain | |
| 5,843,120 A | 12/1998 | Israel et al. | |
| 5,843,180 A | 12/1998 | Jaffe et al. | |
| 5,843,181 A | 12/1998 | Jaffe et al. | |
| 5,849,034 A | 12/1998 | Schwartz | |
| 5,851,228 A | 12/1998 | Pinheiro | |
| 5,855,597 A | 1/1999 | Jayaraman | |
| 5,855,600 A | 1/1999 | Alt | |
| 5,865,723 A | 2/1999 | Love | |
| 5,879,381 A | 3/1999 | Moriuchi et al. | |
| 5,879,382 A | 3/1999 | Boneau | |
| 5,891,190 A | 4/1999 | Boneau | |
| 5,891,191 A | 4/1999 | Stinson | |
| 5,895,407 A | 4/1999 | Jayaraman | |
| 5,895,419 A | 4/1999 | Tweden et al. | |
| 5,899,934 A * | 5/1999 | Amundson et al. | 623/1.11 |
| 5,902,332 A | 5/1999 | Schatz | |
| 5,913,895 A | 6/1999 | Burpee et al. | |
| 5,913,897 A | 6/1999 | Corso et al. | |
| 5,922,020 A | 7/1999 | Klein et al. | |
| 5,922,021 A | 7/1999 | Jang | |
| 5,925,061 A | 7/1999 | Ogi et al. | |
| 5,928,279 A | 7/1999 | Shannon et al. | |
| 5,931,867 A | 8/1999 | Haindl | |
| 5,938,697 A | 8/1999 | Killion et al. | |
| 5,955,145 A | 9/1999 | Kalvala et al. | |
| 5,964,770 A | 10/1999 | Flomenblit et al. | |
| 5,997,973 A | 12/1999 | Bianca, Jr. | |
| 6,013,091 A | 1/2000 | Ley et al. | |
| 6,013,854 A * | 1/2000 | Moriuchi | 623/1.11 |
| 6,017,365 A | 1/2000 | Von Oepen | |
| 6,027,525 A | 2/2000 | Suh et al. | |
| 6,027,527 A | 2/2000 | Asano et al. | |
| 6,042,605 A | 3/2000 | Martin et al. | |
| 6,053,941 A | 4/2000 | Lindberg et al. | |
| 6,059,808 A * | 5/2000 | Boussignac et al. | 606/191 |
| 6,080,192 A | 6/2000 | Demopulos et al. | |
| 6,096,070 A | 8/2000 | Ragheb et al. | |
| 6,120,534 A | 9/2000 | Ruiz | |
| 6,120,847 A | 9/2000 | Yang et al. | |
| 6,132,461 A | 10/2000 | Thompson | |
| 6,139,573 A | 10/2000 | Sogard et al. | |
| 6,159,237 A | 12/2000 | Alt et al. | |
| 6,159,239 A * | 12/2000 | Greenhalgh | 623/1.13 |
| 6,162,537 A | 12/2000 | Martin et al. | |
| 6,179,868 B1 | 1/2001 | Burpee et al. | |
| 6,183,353 B1 | 2/2001 | Frantzen | |
| 6,187,034 B1 | 2/2001 | Frantzen | |
| 6,187,095 B1 | 2/2001 | Labrecque et al. | |
| 6,190,403 B1 | 2/2001 | Fischell et al. | |
| 6,190,406 B1 | 2/2001 | Duerig et al. | |

(56) References Cited

U.S. PATENT DOCUMENTS

| | | | |
|---|---|---|---|
| 6,190,407 B1 | 2/2001 | Ogle et al. | |
| 6,193,747 B1 | 2/2001 | Von Oepen | |
| 6,197,048 B1 | 3/2001 | Richter | |
| 6,197,049 B1 | 3/2001 | Shaolian et al. | |
| 6,221,098 B1 | 4/2001 | Wilson et al. | |
| 6,224,625 B1 | 5/2001 | Jayaraman | |
| 6,231,598 B1 | 5/2001 | Berry et al. | |
| 6,238,401 B1 | 5/2001 | Richter | |
| 6,240,615 B1 | 6/2001 | Kimes et al. | |
| 6,241,762 B1 | 6/2001 | Shanley | |
| 6,251,059 B1 | 6/2001 | Apple et al. | |
| 6,251,134 B1 | 6/2001 | Alt et al. | |
| 6,258,116 B1 | 7/2001 | Hojeibane | |
| 6,258,117 B1 | 7/2001 | Camrud et al. | |
| 6,264,689 B1 | 7/2001 | Colgan et al. | |
| 6,273,910 B1 | 8/2001 | Limon | |
| 6,287,333 B1* | 9/2001 | Appling et al. | 623/1.22 |
| 6,299,604 B1 | 10/2001 | Ragheb et al. | |
| 6,299,755 B1 | 10/2001 | Richter | |
| 6,309,411 B1 | 10/2001 | Lashinski et al. | |
| 6,312,459 B1 | 11/2001 | Huang et al. | |
| 6,315,794 B1 | 11/2001 | Richter | |
| 6,319,277 B1* | 11/2001 | Rudnick et al. | 623/1.13 |
| 6,331,188 B1* | 12/2001 | Lau et al. | 623/1.13 |
| 6,340,367 B1 | 1/2002 | Stinson et al. | |
| 6,344,053 B1 | 2/2002 | Boneau | |
| 6,348,065 B1 | 2/2002 | Brown et al. | |
| 6,355,039 B1 | 3/2002 | Troussel et al. | |
| 6,355,059 B1* | 3/2002 | Richter et al. | 623/1.17 |
| 6,364,904 B1* | 4/2002 | Smith | 623/1.22 |
| 6,383,213 B2 | 5/2002 | Wilson et al. | |
| 6,387,120 B2 | 5/2002 | Wilson et al. | |
| 6,398,803 B1 | 6/2002 | Layne | |
| 6,409,753 B1 | 6/2002 | Brown et al. | |
| 6,416,538 B1 | 7/2002 | Ley et al. | |
| 6,428,569 B1 | 8/2002 | Brown | |
| 6,440,162 B1 | 8/2002 | Cox et al. | |
| 6,464,719 B2 | 10/2002 | Jayaraman | |
| 6,471,980 B2 | 10/2002 | Sirhan et al. | |
| 6,478,815 B1 | 11/2002 | Alt | |
| 6,485,508 B1 | 11/2002 | McGuiness | |
| 6,503,270 B1* | 1/2003 | Richter et al. | 623/1.15 |
| 6,505,654 B1 | 1/2003 | Andersen et al. | |
| 6,506,211 B1 | 1/2003 | Skubitz et al. | |
| 6,506,408 B1 | 1/2003 | Palasis | |
| 6,511,505 B2 | 1/2003 | Cox et al. | |
| 6,527,801 B1 | 3/2003 | Dutta | |
| 6,530,934 B1 | 3/2003 | Jacobsen et al. | |
| 6,530,950 B1 | 3/2003 | Alvarado et al. | |
| 6,540,774 B1 | 4/2003 | Cox | |
| 6,540,775 B1 | 4/2003 | Fischell et al. | |
| 6,558,414 B2 | 5/2003 | Layne | |
| 6,562,065 B1 | 5/2003 | Shanley | |
| 6,565,507 B2 | 5/2003 | Kamata et al. | |
| 6,569,180 B1 | 5/2003 | Sirhan et al. | |
| 6,579,310 B1 | 6/2003 | Cox et al. | |
| 6,579,314 B1 | 6/2003 | Lombardi | |
| 6,602,226 B1 | 8/2003 | Smith et al. | |
| 6,602,281 B1 | 8/2003 | Klein | |
| 6,602,282 B1 | 8/2003 | Yang et al. | |
| 6,605,107 B1 | 8/2003 | Klein | |
| 6,607,554 B2 | 8/2003 | Dang et al. | |
| 6,610,086 B1* | 8/2003 | Kock et al. | 623/1.22 |
| 6,638,301 B1 | 10/2003 | Chandrasekaran et al. | |
| 6,645,240 B2 | 11/2003 | Yee | |
| 6,648,911 B1 | 11/2003 | Sirhan et al. | |
| 6,656,218 B1 | 12/2003 | Denardo et al. | |
| 6,656,220 B1 | 12/2003 | Gomez et al. | |
| 6,663,661 B2 | 12/2003 | Boneau | |
| 6,673,102 B1 | 1/2004 | Vonesh et al. | |
| 6,673,106 B2 | 1/2004 | Mitelberg et al. | |
| 6,699,278 B2 | 3/2004 | Fischell et al. | |
| 6,706,061 B1 | 3/2004 | Fischell et al. | |
| 6,709,453 B2 | 3/2004 | Pinchasik et al. | |
| 6,723,119 B2 | 4/2004 | Pinchasik et al. | |
| 6,730,117 B1 | 5/2004 | Tseng et al. | |
| 6,733,536 B1 | 5/2004 | Gellman | |
| 6,736,844 B1* | 5/2004 | Glatt et al. | 623/1.22 |
| 6,767,418 B1 | 7/2004 | Zhang et al. | |
| 6,770,087 B2 | 8/2004 | Layne | |
| 6,790,298 B2 | 9/2004 | Johnson et al. | |
| 6,827,733 B2 | 12/2004 | Boneau | |
| 6,863,757 B1 | 3/2005 | Gonzalez et al. | |
| 6,866,805 B2 | 3/2005 | Hong et al. | |
| 6,866,860 B2 | 3/2005 | Nathan | |
| 6,899,727 B2 | 5/2005 | Armstrong et al. | |
| 6,911,040 B2 | 6/2005 | Johnson | |
| 6,962,604 B2* | 11/2005 | Hijlkema | 623/1.15 |
| 7,060,093 B2 | 6/2006 | Dang et al. | |
| 7,108,714 B1 | 9/2006 | Becker | |
| 7,112,293 B2 | 9/2006 | Dubson et al. | |
| 7,176,344 B2 | 2/2007 | Gustafson et al. | |
| 7,185,677 B2* | 3/2007 | Houston et al. | 138/39 |
| 7,244,116 B2 | 7/2007 | Dubson et al. | |
| 7,329,277 B2* | 2/2008 | Addonizio et al. | 623/1.22 |
| 7,360,542 B2 | 4/2008 | Nelson et al. | |
| 7,441,559 B2 | 10/2008 | Nelson et al. | |
| 7,540,881 B2* | 6/2009 | Meyer et al. | 623/1.35 |
| 7,637,939 B2* | 12/2009 | Tischler | 623/1.22 |
| 7,722,578 B2 | 5/2010 | Arney et al. | |
| 7,722,661 B2* | 5/2010 | Lenz et al. | 623/1.15 |
| 7,846,198 B2* | 12/2010 | Hogendijk | 623/1.22 |
| 7,887,584 B2 | 2/2011 | Richter | |
| 7,901,448 B2* | 3/2011 | Leopold et al. | 623/1.15 |
| 7,914,568 B2* | 3/2011 | Cully et al. | 623/1.13 |
| 7,922,756 B2* | 4/2011 | Lenz et al. | 623/1.15 |
| 7,955,387 B2 | 6/2011 | Richter | |
| 8,236,043 B2* | 8/2012 | Caro et al. | 623/1.15 |
| 8,328,865 B2 | 12/2012 | Bales et al. | |
| 8,460,364 B2 | 6/2013 | Cottone et al. | |
| 8,496,703 B2 | 7/2013 | Richter | |
| 2001/0020184 A1 | 9/2001 | Dehdashtian et al. | |
| 2001/0032009 A1 | 10/2001 | Layne et al. | |
| 2001/0056298 A1 | 12/2001 | Brown et al. | |
| 2002/0004677 A1 | 1/2002 | Jayaraman | |
| 2002/0007212 A1 | 1/2002 | Brown et al. | |
| 2002/0046783 A1 | 4/2002 | Johnson et al. | |
| 2002/0049488 A1 | 4/2002 | Boneau | |
| 2002/0049489 A1 | 4/2002 | Herweck et al. | |
| 2002/0049492 A1 | 4/2002 | Lashinski et al. | |
| 2002/0052649 A1 | 5/2002 | Greenhalgh | |
| 2002/0055770 A1 | 5/2002 | Doran et al. | |
| 2002/0068969 A1 | 6/2002 | Shanley et al. | |
| 2002/0081732 A1 | 6/2002 | Bowlin et al. | |
| 2002/0082680 A1 | 6/2002 | Shanley et al. | |
| 2002/0082682 A1 | 6/2002 | Barclay et al. | |
| 2002/0084178 A1 | 7/2002 | Dubson et al. | |
| 2002/0103529 A1 | 8/2002 | Pinchasik et al. | |
| 2002/0107560 A1 | 8/2002 | Richter | |
| 2002/0116044 A1* | 8/2002 | Cottone et al. | 623/1.2 |
| 2002/0116049 A1 | 8/2002 | Girton et al. | |
| 2002/0120327 A1 | 8/2002 | Cox et al. | |
| 2002/0138136 A1 | 9/2002 | Chandresekaran et al. | |
| 2002/0161319 A1 | 10/2002 | Matsumoto et al. | |
| 2002/0162605 A1 | 11/2002 | Horton, Jr. et al. | |
| 2002/0165603 A1* | 11/2002 | Thornton et al. | 623/1.13 |
| 2002/0177893 A1 | 11/2002 | Brown et al. | |
| 2003/0017208 A1 | 1/2003 | Ignatious et al. | |
| 2003/0040803 A1 | 2/2003 | Rioux et al. | |
| 2003/0045926 A1 | 3/2003 | Pinchasik | |
| 2003/0050691 A1 | 3/2003 | Shifrin et al. | |
| 2003/0069633 A1* | 4/2003 | Richter et al. | 623/1.22 |
| 2003/0083646 A1 | 5/2003 | Sirhan et al. | |
| 2003/0120197 A1 | 6/2003 | Kaneko et al. | |
| 2003/0130721 A1 | 7/2003 | Martin et al. | |
| 2003/0208260 A1 | 11/2003 | Lau et al. | |
| 2003/0211135 A1 | 11/2003 | Greenhalgh et al. | |
| 2003/0212449 A1 | 11/2003 | Cox | |
| 2004/0044401 A1* | 3/2004 | Bales et al. | 623/1.22 |
| 2004/0064180 A1 | 4/2004 | Boneau | |
| 2004/0072124 A1 | 4/2004 | Kaufman et al. | |
| 2004/0082989 A1 | 4/2004 | Cook et al. | |
| 2004/0088043 A1 | 5/2004 | Klein | |
| 2004/0098095 A1 | 5/2004 | Burnside | |

(56) References Cited

U.S. PATENT DOCUMENTS

| | | | |
|---|---|---|---|
| 2004/0102833 A1 | 5/2004 | Girton et al. | |
| 2004/0106980 A1 | 6/2004 | Solovay et al. | |
| 2004/0193251 A1 | 9/2004 | Rudnick et al. | |
| 2004/0199242 A1 | 10/2004 | Hong et al. | |
| 2004/0230291 A1 | 11/2004 | Richter | |
| 2004/0236402 A1 | 11/2004 | Layne | |
| 2004/0254419 A1 | 12/2004 | Wang et al. | |
| 2004/0255096 A1 | 12/2004 | Norman | |
| 2004/0267349 A1 | 12/2004 | Richter | |
| 2005/0033399 A1 | 2/2005 | Richter | |
| 2005/0084407 A1 | 4/2005 | Myrick | |
| 2005/0107864 A1 | 5/2005 | Hong et al. | |
| 2005/0113888 A1 | 5/2005 | Jimenez et al. | |
| 2005/0131515 A1* | 6/2005 | Cully et al. | 623/1.13 |
| 2005/0209679 A1 | 9/2005 | Melsheimer | |
| 2005/0216076 A1* | 9/2005 | Kveen et al. | 623/1.22 |
| 2005/0246010 A1* | 11/2005 | Alexander et al. | 623/1.12 |
| 2005/0261758 A1 | 11/2005 | Rourke et al. | |
| 2005/0278019 A1 | 12/2005 | Gregorich | |
| 2006/0030934 A1* | 2/2006 | Hogendijk et al. | 623/1.22 |
| 2006/0122691 A1 | 6/2006 | Richter | |
| 2006/0149386 A1 | 7/2006 | Clarke et al. | |
| 2006/0178727 A1 | 8/2006 | Richter | |
| 2006/0195177 A1* | 8/2006 | Kaufmann et al. | 623/1.16 |
| 2006/0246210 A1 | 11/2006 | Iki et al. | |
| 2007/0026132 A1 | 2/2007 | Williams et al. | |
| 2007/0073383 A1 | 3/2007 | Yip et al. | |
| 2007/0150046 A1* | 6/2007 | Meyer et al. | 623/1.15 |
| 2007/0208409 A1 | 9/2007 | Quigley | |
| 2007/0219618 A1* | 9/2007 | Cully et al. | 623/1.13 |
| 2007/0219642 A1 | 9/2007 | Richter | |
| 2007/0239264 A1* | 10/2007 | Fliedner | 623/1.16 |
| 2007/0250148 A1* | 10/2007 | Perry et al. | 623/1.11 |
| 2007/0269936 A1 | 11/2007 | Tanaka et al. | |
| 2008/0097582 A1* | 4/2008 | Shanley et al. | 623/1.22 |
| 2008/0215129 A1 | 9/2008 | Venturelli et al. | |
| 2008/0221664 A1 | 9/2008 | Bales et al. | |
| 2008/0319534 A1 | 12/2008 | Birdsall et al. | |
| 2008/0319535 A1 | 12/2008 | Craven et al. | |
| 2009/0012525 A1 | 1/2009 | Buehlmann et al. | |
| 2009/0036976 A1* | 2/2009 | Beach et al. | 623/1.22 |
| 2009/0062903 A1 | 3/2009 | Pathak | |
| 2009/0210049 A1* | 8/2009 | Thielen et al. | 623/1.16 |
| 2009/0234433 A1* | 9/2009 | Richter | 623/1.17 |
| 2009/0259294 A1 | 10/2009 | Cully et al. | |
| 2009/0264986 A1 | 10/2009 | Bales et al. | |
| 2009/0306766 A1* | 12/2009 | McDermott et al. | 623/1.16 |
| 2010/0004725 A1* | 1/2010 | Zipse et al. | 623/1.2 |
| 2010/0016949 A1* | 1/2010 | Wack | 623/1.15 |
| 2010/0070024 A1* | 3/2010 | Venturelli et al. | 623/1.22 |
| 2010/0198333 A1* | 8/2010 | Macatangay et al. | 623/1.15 |
| 2010/0256735 A1* | 10/2010 | Morales, Jr. | 623/1.15 |
| 2011/0004290 A1 | 1/2011 | Bales et al. | |
| 2011/0125251 A1* | 5/2011 | Cottone et al. | 623/1.16 |
| 2011/0166641 A1* | 7/2011 | Bales et al. | 623/1.16 |
| 2011/0184507 A1 | 7/2011 | Fischer, Jr. et al. | |
| 2011/0208288 A1* | 8/2011 | Arbefeuille et al. | 623/1.13 |
| 2011/0218615 A1 | 9/2011 | Griswold | |
| 2011/0251668 A1 | 10/2011 | Thompson et al. | |
| 2012/0265288 A1 | 10/2012 | Jones et al. | |
| 2012/0303112 A1* | 11/2012 | Armstrong et al. | 623/1.16 |
| 2013/0090721 A1 | 4/2013 | Bales et al. | |
| 2014/0135904 A1* | 5/2014 | Rowe | 623/1.22 |
| 2014/0358218 A1* | 12/2014 | Mitsudo et al. | 623/1.22 |
| 2014/0379066 A1 | 12/2014 | Burpee et al. | |
| 2015/0045874 A1* | 2/2015 | McMahon et al. | 623/1.22 |

FOREIGN PATENT DOCUMENTS

| | | |
|---|---|---|
| CA | 2092337 | 9/1993 |
| CA | 2281775 | 6/2000 |
| CA | 2370184 | 10/2000 |
| DE | 195 12 066 | 11/1996 |
| DE | 297 08 879 | 9/1997 |
| DE | 197 53 123 | 8/1999 |
| DE | 199 00 411 | 7/2000 |
| DE | 199 57 063 | 8/2001 |
| DE | 102 23 399 | 6/2006 |
| EP | 0 364 787 A1 | 4/1990 |
| EP | 0 480 667 A1 | 4/1992 |
| EP | 0 623 354 | 11/1994 |
| EP | 0 747 498 | 12/1996 |
| EP | 0 775 472 A2 | 5/1997 |
| EP | 0 334 046 | 6/1997 |
| EP | 0 830 853 | 3/1998 |
| EP | 0 888 757 | 1/1999 |
| EP | 0 916 318 | 5/1999 |
| EP | 0 958 794 | 12/1999 |
| EP | 0 970 664 | 1/2000 |
| EP | 0 876 216 | 4/2000 |
| EP | 1 020 166 | 7/2000 |
| EP | 1 129 673 | 9/2001 |
| EP | 1 216 717 A1 | 6/2002 |
| EP | 1 148 843 | 4/2003 |
| EP | 1 477 130 | 11/2004 |
| EP | 1 937 184 B1 | 8/2006 |
| EP | 1 834 606 A1 | 9/2007 |
| EP | 1 997 459 A1 | 12/2008 |
| EP | 2 526 905 A1 | 11/2012 |
| EP | 2 529 706 A1 | 12/2012 |
| FR | 2 758 253 | 7/1998 |
| FR | 2 760 351 | 9/1998 |
| JP | 61-106133 | 5/1986 |
| JP | 01-121064 | 5/1989 |
| JP | 02-047243 | 2/1990 |
| JP | 02-057264 | 2/1990 |
| JP | 2061036 A | 3/1990 |
| JP | 2-174859 | 7/1990 |
| JP | 10-277082 | 7/1990 |
| JP | 03-009746 | 1/1991 |
| JP | 07-188876 | 12/1993 |
| JP | 07-080078 | 3/1995 |
| JP | 07-124263 | 5/1995 |
| JP | 07-188877 | 7/1995 |
| JP | 07-265432 | 10/1995 |
| JP | 08-243107 | 9/1996 |
| JP | 2000-167064 | 6/2000 |
| JP | 2000-000297 | 7/2000 |
| JP | 2001-231867 | 8/2001 |
| JP | 2004-089580 | 3/2004 |
| JP | 2005-522594 | 7/2005 |
| JP | 2007-527734 | 10/2007 |
| NZ | 280547 | 9/1998 |
| NZ | 285241 | 3/1999 |
| NZ | 331532 | 1/2000 |
| WO | WO 83/00997 | 3/1983 |
| WO | WO 93/13825 | 7/1993 |
| WO | WO 95/03010 | 2/1995 |
| WO | WO 95/23876 | 9/1995 |
| WO | WO 95/26695 | 10/1995 |
| WO | WO 96/26689 | 9/1996 |
| WO | WO 97/07889 | 3/1997 |
| WO | WO 97/25937 | 7/1997 |
| WO | WO 97/32544 | 9/1997 |
| WO | WO 97/33534 A | 9/1997 |
| WO | WO 97/37617 | 10/1997 |
| WO | WO 98/22159 | 5/1998 |
| WO | WO 98/35634 | 8/1998 |
| WO | WO 98/41169 A1 | 9/1998 |
| WO | WO 99/15108 | 4/1999 |
| WO | WO 99/17680 | 4/1999 |
| WO | WO 99/33410 | 7/1999 |
| WO | WO 99/39660 | 8/1999 |
| WO | WO 99/44543 | 9/1999 |
| WO | WO 99/62431 | 12/1999 |
| WO | WO 00/30563 | 6/2000 |
| WO | WO 00/32138 | 6/2000 |
| WO | WO 00/49971 | 8/2000 |
| WO | WO 01/52771 | 7/2001 |
| WO | WO 01/58504 | 8/2001 |
| WO | WO 02/26279 A1 | 4/2002 |
| WO | WO 02/35984 | 5/2002 |
| WO | WO 03/057075 | 7/2003 |

(56) References Cited

FOREIGN PATENT DOCUMENTS

| WO | WO 03/057077 | A1 | 7/2003 | |
|---|---|---|---|---|
| WO | WO 03/082152 | A1 | 10/2003 | |
| WO | WO 03/087443 | | 10/2003 | |
| WO | WO 2004/016197 | | 2/2004 | |
| WO | WO 2004/045454 | | 6/2004 | |
| WO | WO 2004/058100 | | 7/2004 | |
| WO | WO 2005/000152 | | 1/2005 | |
| WO | WO 2005/034806 | A1 | 4/2005 | |
| WO | WO 2005/058202 | | 6/2005 | |
| WO | WO 2005/070337 | | 8/2005 | |
| WO | WO 2005/072653 | | 8/2005 | |
| WO | WO 2005/102220 | | 11/2005 | |
| WO | WO 2005/118971 | | 12/2005 | |
| WO | WO 2006/014969 | | 2/2006 | |
| WO | WO 2007/105088 | | 9/2007 | |
| WO | WO 2008/049045 | A2 | 4/2008 | |
| WO | WO 2008100783 | A2 * | 8/2008 | ............... A61F 2/02 |

OTHER PUBLICATIONS

Office actions and responses of related U.S. Appl. No. 12/243,732 now abandoned: Notice of Abandonment dated Oct. 28, 2010.
Office actions and responses of related U.S. Appl. No. 12/243,741 now U.S. Pat. No. 7,955,387: Supplemental Notice of Allowability dated May 9, 2011; Supplemental Notice of Allowability dated Apr. 29, 2011; Application Summary of Interview with Examiner dated Feb. 28, 2011; Notice of Allowance and Fees Due with Examiner Interview Summary Record dated Jan. 28, 2011; and Amendment and Response to Non-Final Rejection dated Nov. 29, 2010.
Office actions and responses of related U.S. Appl. No. 12/428,347: Examiner Interview Summary dated Jul. 21, 2011; and Non-Final Rejection dated Apr. 27, 2011.
Extended European Search Report dated Jul. 7, 2010 for EP Application No. 10004585.5-1219, 7 pages.
International Search Report and Written Opinion dated Aug. 4, 2010 for PCT Application No. PCT/IB2010/001036, 13 pages.
Singapore Search and Examination dated Sep. 13, 2000, Application No. 9904228-8.
PCT International Search Report, Application No. PCT/US98/19990 dated May 6, 1999.
Office Actions and Responses to Office Actions of related pending U.S. Appl. No. 11/377,769, filed Mar. 15, 2006: Amendment and Response to Final Rejection with Request for Continued Examination dated Sep. 15, 2010 and Final Rejection dated Jun. 15, 2010.
European Search Report dated Dec. 2, 2003, 5 pages from related abandoned Application No. 01125340.8.
European Search Report dated Oct. 25, 2004, 5 pages from related abandoned Application No. 01125341.6.
European Search Report dated Mar. 11, 2005 , 4 pages from related abandoned Application No. 02733008.3.
Supplemental European Search Report dated Sep. 5, 2007, 3 pages from related Application No. EP 04737140.
Supplemental European Search Report dated Aug. 31, 2009, 3 pages from related Application No. EP 07700481.
Extended EP Search Report, Application No. EP 09008421.1 dated Jan. 15, 2010.
Extended EP Search Report, Application No. EP09008420.3 dated Jan. 15, 2010.
Extended EP Search Report, Application No. EP 09008419.5 dated Jan. 15, 2010.
Extended EP Search Report, Application No. EP07733978.6 dated Mar. 17, 2010.
Extended EP Search Report, Application No. EP 07733978.6 / Publication No. EP 1996113, dated Mar. 17, 2010.
EP Search Report dated Jul. 3, 2008, Application No. EP 1751363.
PCT International Search Report and Written Opinion dated Apr. 5, 2005, 10 pages from related PCT Application No. PCT/IB04/02096.
PCT International Search Report dated May 9, 2009, Application No. PCT/IB05/01524 / Published No. WO 05/118971.
PCT International Search Report and Written Opinion dated Jun. 11, 2008, 9 pages from related Application No. PCT/IB2007/000088.
PCT International Search Report, Dec. 8, 2008, 7 pages from co-pending PCT Application No. PCT/IB2007/000632.
International Preliminary Report on Patentability dated Feb. 25, 2010, 8 pages from related Application No. PCT/IB2008/002515.
PCT International Search Report and Written Opinion dated Dec. 3, 2009, 14 pages from related Application No. PCT/IB2008/002515.
GB Search Report under Section 17 of the 1977 Patent Act dated Apr. 8, 2004, 1 pages from related Application No. GB 0402845.2.
Translation of an OA issued by the German Patent and Trademark Office dated Feb. 28, 2008, Application No. DE 19956249.0-43.
Singapore Search and Examination Report dated Sep. 13, 2000, Application No. 9904228-8.
New Zealand Examination Report dated Sep. 8, 1999, Application No. 337652.
BSC Cancellation Proceeding v. Medinol DE 20108764, NIRflex dated Jan. 11, 2005.
BSC Cancellation Proceeding v. Medinol DE 20108765, NIRflex dated Jan. 11, 2005.
Horton et al., "Biomedical Potential of a Zirconium-Based Bulk Metallic Glass" Mat. Res. Soc. Symp. Proc. vol. 754, Materials Research Society, Feb. 14, 2003, http://www.ornl.gov/webworks/cppr/y2001/pres/116372.pdf.
Database WPI Week 200112 Derwent Publications Ltd., London GB; AN 2000-129595 XP002446760 / JP 20000-000297 A (Inoue A) Jan. 7, 2000.
Busch, R. et al., "On the Glass Forming Ability of Bulk Metallic Glass", Materials Science Forum vols. 235-238 (1997) pp. 327-336.
Cahn, R., "Atomic Transport in Amorphous Alloys: An Introduction", J.Vac. Sci, Technol. A (4(6), Nov./Dec. 1986.
Donaldson, J., "Metallic Glasses: A New Class of Electroplated Coatings", Surface Finishing, Jul. 1986.
Duwez, P. "A Typical Example of Metastability: Metallic Glasses", J.Vac. Sci. Technol. B1 (2) Apr.-Jun. 1983.
Fecht, H. et al., "Destabilization and Vitrification of Crystalline Matter", J. Non-Crystalline Solids, 117/118 (1990) 704-707.
Johnson, W.L. et al., "Electronic Structure of Metallic Glasses", Glassy Metals: Magnetic, Chemical, and Structural Properties, CRC press, pp. 65-108.
Johnson, W.L., "Fundamental Aspects of Bulk Metallic Glass formation in Multicomponent Assays", Materials Science Forum, vols. 225-227 (1996) pp. 35-50.
Johnson, W.L., "Bulk Metallic Glasses—A New Engineering Material", current Opinion in Solid State & Materials Science, 1996, 1:383-386.
Johnson, W.L., "Mechanisms of Instability in Crystalline Alloys with Respect to Vitrification", Journal of Less-Common Metals, 145 (1988) 63-80.
Kavesh, S., "Principles of Fabrication", Metallic Glasses, Papers presented at a Seminar of the Materials Science Division of the American Society for Metals, Sep. 18 and 19, 1976.
Kukulka, D., "New Chill-block Melt Spinning Relations to Predict Ribbon Thickness", J. Thermophysics, vol. 10, No. 3, Technical Notes, 1996.
Kung, K. T-Y., "Electrical Characteristics of Amorphous Molybdenum-Nickel Contacts to Silicon", J.Appl. Phys., 55(10), May 15, 1984 pp. 3882-3885.
Liebermann, H., et al., "Technology of Amorphous Alloys", ChemTech, Jun. 1987, pp. 363-367.
Liebermann, H.H., "The Dependence of the Geometry of Glassy Alloy Ribbons on the Chill Bock Melt-Spinning Process Parameters", Materials Science and Engineering, 43 (1980) 203-210.
Takayama, S., et al., "The Analysis of Casting Conditions of Amorphous Alloys", J. Appl. Phys. 50 (7), Jul. 1979, pp. 4962-4965.
Thakoor, A.P. et al., "Influence of the Microstructure on the Corrosion Behavior of Magnetron Sputter-Quenched Amorphous Metal Alloys", J. Vac. Sci. Technol. A 1 (2), Apr.-Jun. 1983, pp. 520-523.
Williams, R.M. et al., "Corrosion Behavior of Magnetron Sputter-Deposited $[Mo_{0.6}Ru_{0.4}]B_{18}$ and $Mo_{82}B_{18}$ Amorphous Metal Films", J. Electrochemical Soc., vol. 131 No. 12, pp. 2791-2794.

(56) References Cited

OTHER PUBLICATIONS

Zhu, M.F. et al., "Electrical Characteristics of Amorphous $Ni_{36}W_{64}$ Contacts on SI", Advanced Semiconductor Processing and Characterization of Electronic and Optical Materials, Proceedings of SPIE, vol. 463, Jan. 24-25, 1984.
Zhu, M. F., et al., "Investigation of Amorphous $W_{60}Zr_{40}$ Film as a Diffusion Barrier in Metallization Schemes", Phys. Stat. Sol. (a) S6, 471 (1984).
"Technology: Hot Alloy" [online]. Forbes Magazine, Sep. 30, 2002[retrieved Feb. 19, 2003] Retrieved from the internet: <URL:www.forbes.com/global/2002/0930/128.html>.
"Innovative Material is Stronger than Titanium but can be formed like a Plastic" [online]. Jobwerx Manufacturing Network. [retrieved Feb. 19, 2003]. Retrieved from the internet: <URL:www.jobwerx.com/news/archives/LiquidmetalAlloys.com>.
"Liquidmetal Medical Devices" [online], Liquidmetal Technologies, [retrieved Feb. 20, 2003]. Retrieved from the internet: <URL:www.liquidmetal.com/applications/dsp.medical.asp>.
"Liquidmetal Technology Reborn in LMG" [online]. Golfweb, Jul. 31, 2002 [retrieved Feb. 20, 2003]. Retrieved from the internet: <URL:www.golfweb.com/u/cd/multi/0,1977m5564401,00.html>.
"Choosing the right suture material" [online], The Royal College of Surgeons of Edinburgh [retrieved Mar. 5, 2003]. Retrieved from the internet <URL:www.edu.rcsed.ac.uk/lectures/lt5.htm>.
"BBC health—Ask the Doctor—Heart Valves Replacement" [online]. BBC health homepage, Jul. 18, 2001. [retrieved Mar. 12, 2003]. Retrieved from the internet: <URL:www.bbc.co.uk/health/ask_doctor/heartvalve_replacement.shtml>.
"Artificial Organs Cardiovascular" [online]. National University of Singapore. [retrieved Feb. 12, 2003]. Retrieved from the internet <URL:www.scholars.nus.edu.sg/cpace/prosthesis/stein/cardio.html>.
"Heart replacement valves" [online]. Research Defense Society. [retrieved Mar. 12, 2003]. Retrieved from the internet: <URL:www.rds-online.org.uk/milestones/valves.html>.
"Material considerations in Replacement Heart Valves" [online]. Rose-Hulman Institute of Technology Fall 1996 [retrieved Mar. 12, 2003]. Retrieved from the internet: <URL:www.rose-hulman.edu/class/scheme/HTML/SiteMap/Undergraduate/StudentProjects/MaterialsStudentProjects/heart/heart.html>.
"The Physics Behind Artificial Heart Valves" [online]. Claire Carson, et al., Dec. 4, 2000 [retrieved Mar. 12, 2003] Retrieved from the internet: <URL:www.ipass.net/~tonyg/HeartValvesWeb.html>.
"Medical Dictionary—Artificial Heart Valve" [online]. Dr. Malcolm C. Brown, 2000 [retrieved on Mar. 12, 2003]. Retrieved from the internet: <URL:http://www.thebrowns23.freeserve.co.uk/entries/ARTIFICIAL_HEART_VALVE>.
Jostent Peripheral Stent Graft [online]. JOMED 2002, [retrieved Mar. 14, 2003]. Retrieved from the internet: <URL:www.jomed.com/products/jpsg/productinfo/jostent-psg.html>.
"Recent Advances in Titanium Wire Technology", [online]. TP Orthodontics, Inc. Jan. 1999 [retrieved Mar. 15, 2003]. Retrieved from the internet: <URL:http://www.tportho.com/doctorsroom/whitepapers/pdf/titanium.pdf>.
"Dental Implants" [online]. Niagara Oral Surgery [retrieved on Mar. 17, 2003] <URL:www.niagaraoralsorgery.com/ser implants.htm>.
"Lecture 11—Metals for Implantation", [online]. Wayne State University, [retrieved Mar. 17, 2003]. Retrieved from the internet: <URL:http://ttb.eng.wayne.edu/~grimm/BME5370/Lect11Out.html>.
"Investment Materials" [online]. Guy's, King's College & St. Thomas's Hospital Dental Institute, Dental Biomaterials Science, R.V. Curtis [retrieved Mar. 15, 2003]. Retrieved from the internet: <URL:http://r-curtis.umds.ac.uk/bds3a/investment%20materials%201.htm>.
"Metal Casting Alloys" [online]. Guy's, King's College & St. Thomas's Hospital Dental Institute, Dental Biomaterials Science, R.V. Curtis [retrieved on Mar. 15, 2003]. Retrieved from the internet: <URL:http://r-curtis.umds.ac.uk/bds3a/BMCalloys.HTM>.

"Metals & Alloys" [online]. Guy's, King's College & St. Thomas's Hospital Dental Institute, Dental Biomaterials Science, R.V. Curtis, [retrieved on Mar. 15, 2003]. Retrieved from the internet: <URL:http://r-curtis.umds.ac.uk/bds3a/metallurgy.HTM>.
"TP Original Wire: Development of a High-Performance Orthodontic Wire", [online]. TP Orthodontics, Inc. 1998 [retrieved on Mar. 15, 2003]. Retrieved from the internet: <URL:http://www.tportho.com.br/doctorsroom/whitepapers/pdforiginalwire.pdf>.
"Metallic Glasses Bulk Up", [online]. Mechanical Engineering Magazine, Jun. 1998. [retrieved on Mar. 21, 2003]. Retrieved from the internet: <URL:www.memagazine.org/backissues/june98/features/metallic/metallic.html>.
"Hasta La Vista, Titanium", [online]. Business 2.0, Oct. 2002. [retrieved on Mar. 21, 2003]. Retrieved from the internet: <URL:www.business2.com/articles/mag/print/0,1643,43538,00.html>.
"New metal alloy is super strong", [online]. You magazine. [retrieved on Mar. 21, 2003]. Retrieved on the internet: <URL:www.yo.com.au/news/1022.htm>.
"Lessons of the Björk-Shiley Heart Valve Failure, Mechanics of Heart Valves" [online]. University of Texas at Austin. [retrieved on Mar. 25, 2003]. Retrieved from the internet: <URL:www.me.utexas.edu/~uer/heartvalves/mechanics.html>.
Atzmon, M. et al., "Study of Amorphouse Phases Formed by Solid-State Reaction in Elemental Composites", Rapidly Quenched Metals, Proceedings of the Fifth International Conference on Rapidly Quenced Metals, Würzburg, Germany, Sep. 3-7, 1984.
Office Actions and Responses to Office Actions of related co-pending U.S. Appl. No. 11/377,769, filed Mar. 15, 2006: Amendment and Response to Final Rejection with Request for Continued Examination dated Sep. 15, 2010; Final Rejection dated Jun. 15, 2010; Amendment and Response to Non-Final Rejection dated Mar. 24, 2010; Non-Final Rejection dated Dec. 24, 2009; Amendment and Reponse to Restriction Requirement Sep. 28, 2009; and Requirement for Restriction/Election dated Aug. 27, 2009.
Office Actions and Responses to Office Actions of related abandoned U.S. Appl. No. 10/860,735, filed Jun. 3, 2004: Notice of Abandonment dated Jun. 6, 2007; Examiner Interview Summary Record dated Apr. 4, 2007; Non-Final Rejection dated Oct. 11, 2006; Response to Election/Restriction Requirement with Extension of Time dated Aug. 11, 2006; and Requirement for Restriction/Election dated Apr. 11, 2006.
Office Actions and Responses to Office Actions of related co-pending U.S. Appl. No. 11/331,639, filed Jan. 13, 2006: Amendment and Response to Final Rejection with Request for Continued Examination dated Aug. 4, 2010; Examiner Interview Summary dated Jun. 29, 2010; Final Rejection dated May 4, 2010; and Amendment and Response to Non-Final Rejection with Extension of Time dated Feb. 2, 2010.
Office Actions and Responses to Office Actions of related co-pending U.S. Appl. No. 10/607,604, filed Jun. 27, 2003: Notice of Abandonment dated Jun. 4, 2009; Final Rejection dated Dec. 3, 2008; Amendment and Response to Non-Final Rejection with Extension of Time dated Nov. 13, 2007; Non-Final Rejection dated Jul. 12, 2007; Amendment and Response to Non-Final Rejection with Request for Continued Examination & Extension of Time dated May 2, 2007; Final Rejection dated Nov. 6, 2006; Amendment and Response to Non-Final Rejection with Extension of Time dated Aug. 11, 2006; Non-Final Rejection dated May 1, 2006; Request for Continued Examination & Extension of Time dated Apr. 7, 2006; Advisory Action dated Mar. 31, 2006; Amendment and Response to Notice of Non-Compliance dated Sep. 15, 2005; Notice of Non-Compliant or Non-Responsvice Amendment dated Aug. 24, 2005; Amendment and Response to Non-Final Rejection dated May 18, 2005; Non-Final Rejection dated Feb. 23, 2005; Response to Restriction Requirement dated Dec. 17, 2004; and Requirement for Restriction/Election dated Nov. 17, 2004.
Office Actions and Responses to Office Actions of related co-pending U.S. Appl. No. 12/243,723, filed Oct. 1, 2008: Amendment and Response to Final Rejection with Request for Continued Examination dated Jul. 7, 2010; Final Rejection dated Apr. 7, 2010; Amendment and Response to Non-Final Rejection dated Dec. 18, 2009; and Non-Final Rejection dated Sep. 18, 2009.

(56) References Cited

OTHER PUBLICATIONS

Office Actions and Responses to Office Actions of related co-pending U.S. Appl. No. 12/243,732, filed Oct. 1, 2008: Examiner Interview Summary Record dated Jun. 29, 2010; Final Rejection dated Apr. 9, 2010; Amendment and Response to Non-Final Rejection with Extension of Time dated Jan. 20, 2010; and Non-Final Rejection dated Sep. 21, 2009.

Office Actions and Reponses to Office Actions of related abandoned U.S. Appl. No. 09/204,830, filed Dec. 3, 1998: Notice of Abandonment dated Oct. 1, 2002; Request for Extension of Time dated Apr. 5, 2002; Final Rejection dated Dec. 11, 2001; Amendment and Response after Non-Final Rejection dated Oct. 10, 2001; Non-Final Rejection dated Sep. 10, 2001; Advisory Action dated Jul. 18, 2001; Amendment and Response after Final Rejection dated Jul. 11, 2001; Final Rejection dated May 11, 2001; Amendment and Response after Non-Final Rejection with Extension of Time dated Mar. 7, 2001; Non-Final Rejection dated Sep. 18, 2000; Continuing Prosecution Application dated Aug. 16, 2000; Advisory Action dated Jul. 31, 2000; Amendment after Final Rejection dated Jul. 3, 2000; Final Rejection dated May 5, 2000; Reponse after Non-Final Rejection dated Jan. 31, 2000; and Non-Final Rejection dated Aug. 3, 1999.

Office Actions and Reponses to Office Actions of related abandoned U.S. Appl. No. 10/116,159, filed Apr. 5, 2002: Notice of Abandonment dated Jan. 25, 2005; Advisory Action dated Jul. 20, 2004; Amendment and Response after Final Rejection dated Jun. 30, 2004; Final Rejection dated Jun. 8, 2004; Amendment and Response after Non-Final Rejection dated Mar. 24, 2004; Non-Final Rejection dated Dec. 1, 2003; Response to Restriction/Election Requirement dated Sep. 17, 2003; and Requirement for Restriction/Election dated Aug. 26, 2003.

Office Actions and Reponse to Office Actions of related U.S. Appl. No. 12/243,741, filed Oct. 1, 2008: Non-Final Rejection dated Sep. 30, 2010.

Extended European Search Report and Opinion from corresponding EP Application No. 12181899.1-2320 dated Oct. 1, 2012, 6 pages.

Office Actions and Responses of Related U.S. Appl. No. 11/331,639; Amendment and Response to Final Rejection with Request for Continued Examination dated Aug. 4, 2010; Examiner Interview Summary dated Jun. 29, 2010; Final Rejection dated May 4, 2010; and Amendment and Response to Non-Final Rejection with Extension of Time dated Feb. 2, 2010.

Office Actions and Responses of Related U.S. Appl. No. 11/729,516; Non-Final Rejection dated Sep. 20, 2011.

Office Actions and Response of Related U.S. Appl. No. 11/377,769; Non-Final Rejection dated Aug. 1, 2011.

Office Actions and Responses of related U.S. Appl. No. 13/096,561: Response to Non-Final Rejection and Terminal Disclaimer dated Nov. 16, 2012; and Non-Final Rejection dated Aug. 16, 2012.

Office Actions and Responses of related U.S. Appl. No. 12/428,347: Notice of Allowance dated Oct. 2, 2012; Supplemental Amendment dated May 9, 2012; and Amendment and Response to Non-Final Rejection dated Mar. 22, 2012.

Office Actions and Responses of related U.S. Appl. No. 11/729,516: Applicant Initiated Interview Summary and Office Action Appendix dated May 4, 2012; Amendment and response to Final Rejection with RCE dated May 1, 2012; Final Rejection dated Feb. 1, 2012; and Amendment and Response to Non-Final Rejection dated Dec. 20, 2011.

Extended European Search Report from corresponding EP Application No. 12176459.1-2320 dated Oct. 31, 2012, 7 pages.

Office Actions and Response of related U.S. Appl. No. 11/377,769: Amendment and Response to Final Rejection with RCE dated Apr. 13, 2012.

Office Actions and Responses of Related U.S. Appl. No. 11/377,769: Final Rejection dated Jan. 13, 2012.

Office Actions and Responses of Related U.S. Appl. No. 12/428,347: Non-Final Rejection dated Dec. 23, 2011.

Office Actions and Responses of Related U.S. Appl. No. 11/729,516: Final Rejection dated Feb. 1, 2012.

Extended European Search Report for corresponding EP Application No. 12187494.5-2320 dated Nov. 15, 2012, 6 pages.

International Search Report and Written Opinion from PCT Application No. PCT/IB2014/001121 dated Oct. 15, 2014, 11 pages.

\* cited by examiner

HELICAL HYBRID STENT

This application claims the benefit of U.S. application Ser. No. 12/428,347, filed on Apr. 22, 2009, the entire content of which is incorporated by reference.

FIELD OF THE INVENTION

The invention relates generally to stents, which are intraluminal endoprosthesis devices implanted into vessels within the body, such as blood vessels, to support and hold open the vessels, or to secure and support other endoprostheses in vessels.

BACKGROUND OF THE INVENTION

Various stents are known in the art. Typically, stents are generally tubular in shape, and are expandable from a relatively small, unexpanded diameter to a larger, expanded diameter. For implantation, the stent is typically mounted on the end of a catheter with the stent being held on the catheter in its relatively small, unexpanded diameter. Using a catheter, the unexpanded stent is directed through the lumen to the intended implantation site. Once the stent is at the intended implantation site, it is expanded, typically either by a balloon or by allowing the stent to self-expand. In either case, the expanded stent resists the tendency of the vessel to narrow, thereby maintaining the vessel's patency.

Stents may be constructed from tubes or from a flat sheet of metal, which is rolled and fixed such as by welding, mechanical lock or otherwise, to form the tubular structure of the stent.

Some examples of patents relating to stent designs include U.S. Pat. No. 4,733,665 to Palmaz; U.S. Pat. Nos. 4,800,882 and 5,282,824 to Gianturco; U.S. Pat. Nos. 4,856,516 and 5,116,365 to Hillstead; U.S. Pat. Nos. 4,886,062 and 4,969,458 to Wiktor; U.S. Pat. No. 5,019,090 to Pinchuk; U.S. Pat. No. 5,102,417 to Palmaz and Schatz; U.S. Pat. No. 5,104,404 to Wolff; U.S. Pat. No. 5,161,547 to Tower; U.S. Pat. No. 5,383,892 to Cardon et al.; U.S. Pat. No. 5,449,373 to Pinchasik et al.; and U.S. Pat. No. 5,733,303 to Israel et al.

One type of stent is known as the helical or coiled stent. Such stent designs are described in, for example, U.S. Pat. Nos. 6,503,270 and 6,355,059, incorporated herein, in toto, by reference. This stent design is configured as a helical stent in which the coil is formed from a wound strip of cells wherein the cells form a serpentine pattern comprising a series of bends. Other similar helically coiled stent structures are known in the art.

Prior stent designs have focused on providing sufficient radial strength when it is expanded so that it can sufficiently support the lumen. Stents with high radial strength, however, tend also to be more longitudinally stiff than the vessel in which it is implanted. When the stent is more longitudinally stiff than the vessel in which it is implanted, increased trauma to the vessel may occur at the ends of the stent, due to stress concentrations on account of the mismatch in compliance between the stented and un-stented sections of the vessel, or otherwise. In addition, the stent may interfere with the vessel's natural tendency to bend and to stretch. Conversely, stents with good flexibility often lack sufficient and/or uniform radial support for the vessel wall. Thus, a continued need exists in the art for a stent having a balance of good radial strength and a high degree of longitudinal flexibility.

Another problem in the art arises when trying to simplify the manufacturing process of a stent to reduce costs yet prevent manufacturing defects, while still producing a stent with uniformly high flexibility and sufficient radial support.

SUMMARY OF THE INVENTION

The present invention provides a helical stent for intravascular use that is longitudinally flexible such that it can easily be tracked down a tortuous lumen while conforming to the contours of the vessel and provide uniform support to the vessel after deployment. The stent of the invention comprises a main stent component and a second stent component. The main stent component may be of a metal or amorphous metal alloy material. With an amorphous metal stent, the stent has the radial support of a conventional metal stent combined with longitudinal flexibility, conformability and fatigue resistance to repeated longitudinal bending, compression and twisting which may be higher than that achievable by metal stents.

Upon formation into a stent, the main stent component forms a tubular structure of helical windings at an oblique angle to the longitudinal axis of the stent. The helical windings extend at least along the central portion of the stent. Each winding may be spaced apart from the adjacent winding, or may be nestled in the adjacent winding. The distance along the longitudinal axis of the stent between the windings may be varied depending on the needs of the particular stent. Before it is helically wound to form a tubular stent, the main stent component is a flat ribbon or strip, which is defined by undulations (e.g., sinusoidal, zig-zag) or a patterned band of cells (e.g., hexagonal or other like-geometric structure). The strip is composed of one or more side bands that wind helically along the length of the stent, as well as end bands extending from either or both ends of the side bands, positioned at an angle to the side bands. The end bands are configured to form a right cylinder to the longitudinal axis of the stent at either or both ends of the formed stent. The side bands and end bands are understood to include portions having, for example, a generally sinusoidal, zig-zag, hexagonal or other like geometric structure.

In one embodiment of the invention, the main stent component may have one or more struts, which are sufficiently wide to include one or more full or partial fenestrations. The fenestrated struts may be connected by loops or turns whose width is narrower than that of the fenestrated struts to provide enhanced flexibility in the loops or turns.

In another embodiment, the main stent component may be designed such that each helical winding is nestled next to an adjacent helical winding of the helical structure so that the space between the windings is minimized; that is, one winding is nestled into an adjacent, substantially similar winding as the side band ribbon travels diagonally around the circumference of the stent. In this manner, the helical windings of the stent provide enhanced coverage of the wall of the lumen without loss of overall stent flexibility. Because the helical windings may be nestled into one another without directly touching each other, the overall flexibility of the formed stent is unaffected by the proximity of adjacent windings of the helical coils.

The second stent component, i.e., a securement, functions to maintain the tubular shape of the main stent component while aiding in longitudinal flexibility. The securement provides structural support to the stent. The securement is oriented and affixed to the main stent component such that, upon expansion or bending of the stent, the securement contributes to the overall flexibility of the stent while still maintaining the main stent component in a tubular shape. The securement may comprise fibers, wires, threads, ribbons, strips, polymers, meshes or the like.

DETAILED DESCRIPTION OF THE INVENTION

Figure 1:
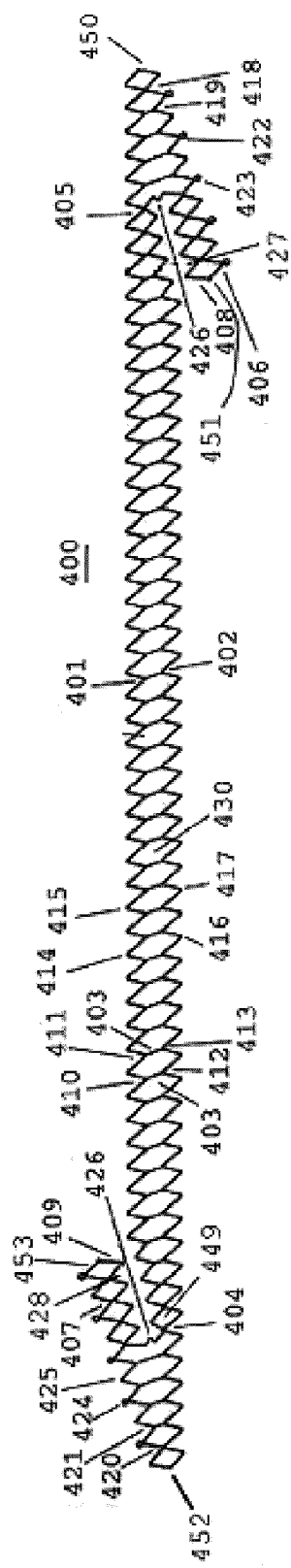
FIG. 1 illustrates a main stent component composed of a flat ribbon with a patterned band according to one embodiment of the invention.

This invention provides a new class of intraluminal prosthetic devices defined as helical hybrid stents. As further explained below, the stents of the invention comprise a main stent component in the form of a helical tubular structure, which may be held in the tubular shape by a second stent component, i.e., a securement. The main stent component is formed from a continuous undulating or patterned strip helically wound to form a helical stent. The strip has end sections that form cylindrical rings in the tubular helical stent. As such, one inventive feature is the central body of the stent having a spiral structure which is flanked by cylindrical rings at both ends of the stent. The strip forming the central body portion comprises one or more side bands each having undulations while the ends sections comprise one or more end bands each having undulations. Each end band is connected to a side band at an angle offset to the side band and may extend back toward the side band. The lengths of struts forming the undulations of the side or end bands may be uniform or variable to assist in the helical winding. The side and end bands may be connected to one another by cross-struts. The length and shape of the cross-struts may be varied across the length of the strip, and the cross-strut may contain one or more loops. The undulations of the helically wound stent may be nestled next to an adjacent helical undulation to promote uniform coverage. The main stent component may be formed of any conventional metallic substance or an amorphous metal alloy.

In any of the novel helical stents herein, the main stent component may also include struts having full or partial fenestrations of any suitable shape and size in the side and/or end bands. Fenestrations allow the deposit of a therapeutic agent with clinical benefits within the recesses of the helical stent. The stent may be configured with struts of sufficient width to accommodate the fenestrations and loops connecting the struts of sufficiently narrow dimensions to accommodate bending and expansion of the resulting stent.

The main stent component, with or without fenestrations or nestling, may be held in place by another inventive feature, i.e., the securement. The securement may comprise any form of polymer, fibers, wires, threads, bands, ribbons, meshes or sheets affixed to the main stent component by any of a variety of means known in the art, such as, for example, welding, bonding, embedding, braiding, weaving, crimping, tying, press-fitting or injection into a mold with the main stent component, also including joining by adhesive means, e.g., gluing, dip coating, spray coating, or the like. The securement may be oriented circumferentially, helically, longitudinally or otherwise and may be affixed to or embedded in a portion or the entirety of the main stent component such that, upon expansion or bending of the stent, the securement facilitates the overall flexibility of the stent while still maintaining the main stent component in a tubular shape.

The main stent component may be formed and patterned from a strip using methods known in the art or described herein. FIG. 1 illustrates an embodiment of the invention wherein the main stent component is formed as a patterned band, shown in an uncoiled state, i.e., flat. As depicted in FIG. 1, the pattern of the ribbon comprises a single row of cells 430, defined by an interconnected first side band 401 with undulations and a second side band 402 with undulations. Also, end bands 406 and 407 extend at an oblique angle to side bands 401 and 402. As the main stent component is formed into a tubular shape, the row of cells 430 take on a continuous helical winding along the central portion of the longitudinal axis of the stent while end bands 406 and 407 form a right cylindrical shape at each end of the stent. The formation of the tubular helical central body portion from a flat patterned band in this manner is distinguished from the process where the design is formed from a pre-existing tubular material.

In FIG. 1, the first side band 401 and second side band 402 extend in a generally parallel orientation except at either end of the side bands where the first side band tapers toward the second side band and the second side band tapers toward the first side band. As depicted in FIG. 1, the undulating pattern of the first side band 401 comprises troughs (e.g., 410, 411) that extend toward the second side band 402 and peaks (e.g., 414, 415) that point away from the second side band 402. Similarly, the undulations of the second side band 402 comprise troughs (e.g., 412, 413) that extend toward the first side band 401 and peaks (e.g., 416, 417) that point away from the first side band 401. Thus, in FIG. 1, the first and second side bands are oriented out-of-phase with each other (troughs substantially aligned with troughs). In other embodiments, the first and second side bands may be in-phase so that the peaks and troughs are substantially aligned.

In FIG. 1, the struts of the side bands defining peaks (416, 417) and troughs (412, 413) have substantially equal lengths in the central strip portion but become shorter as the side bands taper toward each other. In the embodiment of FIG. 1, the first side band 401 and second side band 402 are connected to each other by a plurality of first cross-struts 403, defining a row of cells. Specifically, at least one trough (e.g., 411) of the first side band 401 is connected to a corresponding trough (e.g., 413) of the second side band 402 via a first cross strut 403 in FIG. 1. Thus, in this embodiment, a series of cells are formed, each cell 430 defined individually by the joining of the adjacent side bands to form an enclosed space by cross-struts. For example, a cell in the central strip portion is defined by the portion of the first side band between troughs 410 and 411, the portion of the second side band between troughs 412 and 413 and first cross-struts 403 respectively connecting troughs 410 and 412 and troughs 411 and 413.

In alternative embodiments, the number, length and shape of first cross-struts 403 may differ from that illustrated in FIG. 1. For example, the first cross-struts 403 may connect the first band 401 and second band 402 at regular intervals at, inter alia, every trough, every second trough, every third trough, or every fourth trough, etc., thereby making larger cells or cells with different geometric properties. Also, cross-struts may be omitted and the first side band may be connected directed to the second side band. For example, cell 449 is diamond shaped and defined only by the undulations of the first and second side bands. In other embodiments, the first cross-struts 403 may connect the first side band 401 and second side band 402 at varying, non-regular intervals. Variable, non-regular interval connections may form a variety of differently sized cells along a continuous main stent component as may be appropriate for a particular use. Further, the cross-struts may connect the peaks of the first side band to the trough of the second side band, or the troughs of the first side band to the peaks of the second side band.

The first cross-struts 403 may each have the same width relative to each other and to the side bands 401, 402, as shown in FIG. 1. Alternatively, the first cross-struts 403 may have a different width from the first and second side bands 401, 402, or a different width from each other, as appropriate for a particular use. The cross-struts may connect adjacent or offset troughs of the first and second side bands 401, 402. In addition, first cross-struts 403 may comprise a straight member or may contain one or more loops. As shown in FIG. 1, differently shaped cross-struts, or no cross-struts may alternatively be employed in a single stent design depending on the particular use of the stent so that a stent having different cell shapes may be formed. Exemplary cell shapes are described in U.S. Pat. No. 7,141,062 (triangular cells) or U.S. Pat. No. 5,733,303 (square cells); the disclosure of square and triangular cell structures is incorporated from these patents by reference herein. Square cells have four points of connection as between radially supporting elements while a triangular cell has three points of connection between radially supporting elements. The undulations of the side and end bands provide the radially supporting elements of the invention.

The side bands 401 and 402 of the main stent component 400 in the embodiment depicted in FIG. 1 taper at each end. The length of the cross-struts 403 shorten toward each end of the main stent component 400, so that the first and second side bands 401, 402 become more snugly arranged and eventually are connected directly at points of connection 404 and 405. Alternatively, or in addition to shortened cross-struts, the side bands may taper to one another by reducing the strut lengths in the undulations.

Extending from the end of either or both side bands 401 and 402 in FIG. 1 are end bands 406 and 407. Thus, a first end band 406 extends from the end of the first side band 401 in a direction offset and oblique from the general direction of the first side band 401. In FIG. 1, the first end band extends back in the direction of the first side band at an angle less than 45 degrees to the direction of the first side band when the strip is laid flat. A second end band 407 extends from the end of the second side band 402 in a general direction offset and oblique from the general direction of the second side band 402 and opposite the first end band. In FIG. 1, the second end band also extends back in the direction of the second side band at an angle less than 45 degrees to the direction of the second side band when the strip is laid flat. When forming the tubular stent, end bands 406 and 407 are configured to form right cylinders at the ends of the stent, and flank both ends of the helical winding of the strip. First end band 406 has first edge 450 and second edge 451. In the tubular form, first edge 450 is brought together with second edge 451 to form a right cylinder to the longitudinal axis of the stent. Second end band 403 has first edge 452 and second edge 453. In the tubular form, first edge 452 is brought together with second edge 453 for form a right cylinder to the longitudinal axis of the stent. As further explained below, edge 450 and 451 may be permanently connected, or as an alternative, may be held in position with a securement, which may hold the two edges in close proximity to form a right cylinder to the longitudinal axis of the stent.

The first end band 406 and second end band 407 each contain undulations having struts and loops or turns. The first end band 406 has troughs (e.g., 418, 419) that extend toward the first side band 401 and peaks (e.g., 422, 423) that point away from the first side band 401. Likewise, the second end band 407 has troughs (e.g., 420, 421) that extend toward second side band and peaks (e.g., 424, 425) that point away from the second side band 402. The first end band 406 connects directly to the first side band 401 at, e.g., trough 418; however, as the first end band 406 angularly extends away from the first side band, second cross-struts 426 connect the first end band 406 to the first side band 401. Likewise, the second end band 407 connects directly to the second side band 402 at, e.g., trough 420; however, as the second end band 407 angularly extends away from the second side band, second cross-struts 426 connect the second end band 407 to the second side band 402. As depicted in FIG. 1, the second cross-struts 426 may contain one or more loops between points of connection with adjacent end bands and/or side bands. The peaks of the first end band 406 and second end band 407 optionally may have additional circular structures extending from the peaks (e.g., 423, 424) as depicted by FIG. 1.

In addition, a third end band 408 having undulations is arranged generally parallel to first end band 406, with the troughs of the third end band, e.g., 427, extending toward the first end band and directly connected to said first end band. A fourth end band 409 having undulations is arranged generally parallel to second end band 407, with the troughs of the fourth end band, e.g. 428, extending toward the second end band.

Figure 2:
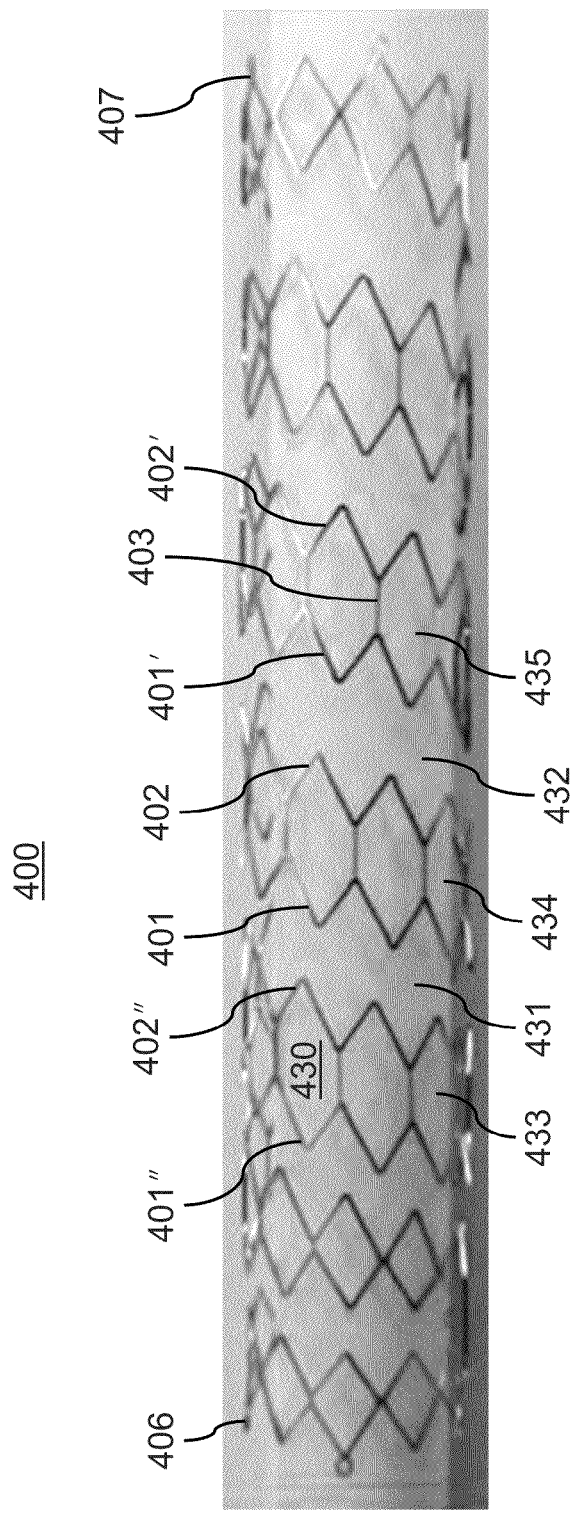
FIG. 2 illustrates a main stent component of a patterned band formed into a tubular shape having a space between adjacent helical windings.

FIG. 2 illustrates the main stent component 400 of FIG. 1 helically wound into a tubular structure. The strip of cells 430 in main stent component 400 forms a helical winding in the central portion in which a cell in one winding is longitudinally-spaced apart from the cell of an adjacent winding. First side band 401 and second side band 402 are connected by cross-struts 403 and are helically wound around the longitudinal axis of the stent so that first and second side bands alternate along the stent's longitudinal axis. In the helically wound stent, as shown in FIG. 2, first side band 401 is adjacent and connected to adjacent second side band 402 by cross strut 403, but is also adjacent and unconnected to the second side band of an adjacent winding 402". Similarly, second side band 402 is unconnected to a longitudinally adjacent first side band 401' in the helical stent. End bands 406 and 407 secure the ends of the tubular structure and form substantial right cylindrical rings relative to the longitudinal axis of the stent. Open spaces, e.g., 431 and 432, exists between adjacent windings, e.g., 433, 434, 435. In FIG. 2, the first and second side bands 401 and 402 are spaced apart either by the presence of the cross-struts, or by the spaced winding of the helical strip. In addition, a securement, as discussed below, may maintain the spacing between the adjacent windings.

Figure 3:
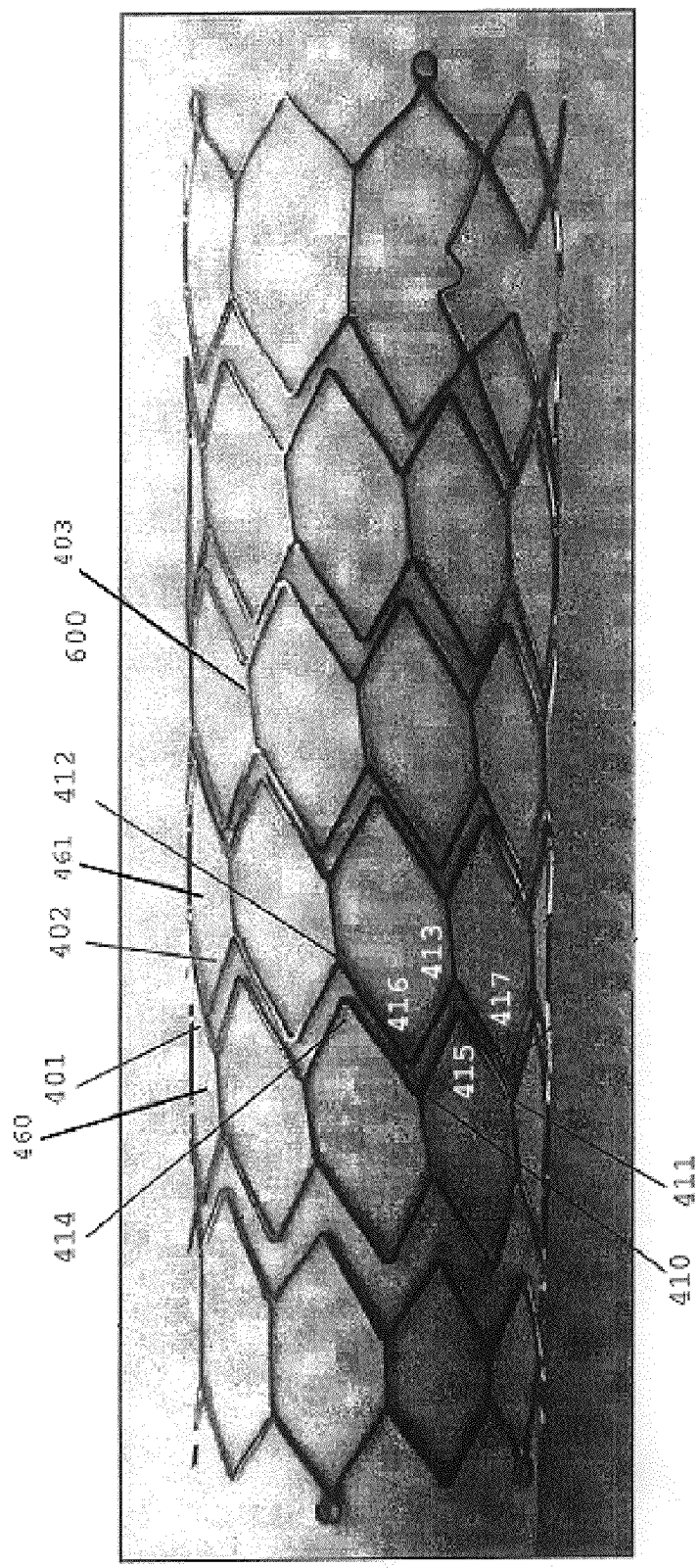
FIG. 3 illustrate another embodiment wherein a helical winding of the main stent component is nestled into an adjacent helical winding.

FIG. 3 illustrates a stent according to another embodiment of the invention wherein the helical windings are positioned so that little or no substantial longitudinal space exists between cycles of the helical coils. That is, as illustrated by FIG. 3, the peaks (e.g. 414, 415) of the first helical winding 460 are nestled toward troughs (e.g. 412, 413) of the second helical winding 461; yet, the first side band 401 remains substantially parallel to the second side band 402. Likewise, the peaks (e.g. 416, 417) of the second helical winding 461 are nestled toward troughs (e.g. 410, 411) of the first helical winding 460. It may be desirable to position the nestled side bands so that no direct contact occurs between first side band 401 and second side band 402. Because the first side band 401 and the second side band 402 are arranged so that the substantially similar but opposite undulations are aligned, the first side band 401 and the second side band 402 can approach one another in this fashion over the entire length of the formed stent. Side bands having struts of identical lengths also aid in nestling. In this manner, the first side band 401 and the second side band 402 may be described as nestled to one another. In FIG. 3, the first and second side bands 401 and 402 are spaced apart only by the presence of the cross-struts. As shown, the distance between the nestled windings is shorter than the length of cross-strut 403. Further, the first side band is nestled toward helically adjacent second side band without direct connection between the first side band and adjacent second side band. The stent of FIG. 3 has the additional advantage that the nestling of adjacent windings minimizes the unsupported areas of the vessel wall and/or securement to prevent sagging of the securement into the lumen upon expansion without any loss of flexibility to the stent, as further discussed below. In addition, the nestling of the helical coils separately may facilitate the maintenance of the structure in the tubular form.

Figure 4A:
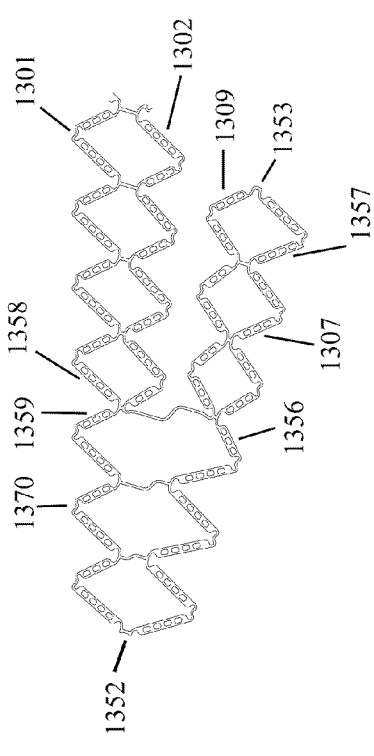
FIG. 4A is an enlarged view of an end band of the main stent component of FIG. 4.
Figure 4:
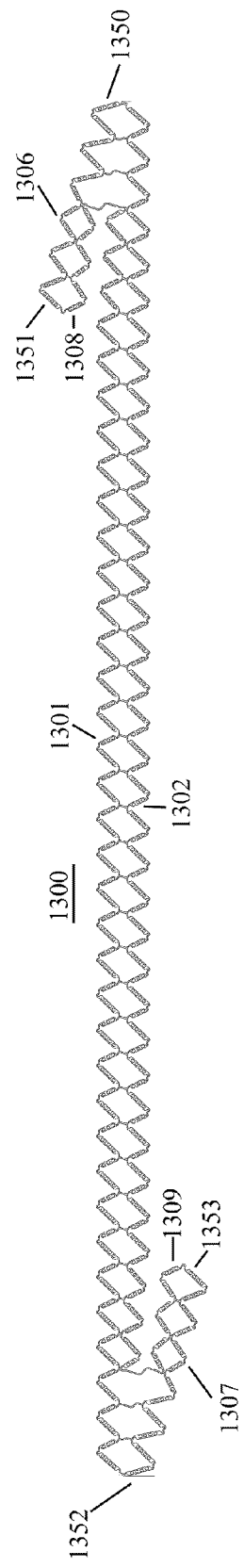
FIG. 4 illustrates an embodiment of a main stent component composed of a flat ribbon having a patterned band and comprises struts with one or more exemplary fenestrations.

FIG. 4 illustrates an alternative embodiment wherein the main stent component 1300 is laid out in flat form, i.e., uncoiled. As depicted, the main stent component 1300 has a patterned band in the longitudinal direction. Like the embodiment of FIG. 1, the design of the main stent component 1300 in FIG. 4 contains a first side band 1301, a second side band 1302, a first end band 1306, a second end band 1307, a third end band 1308 and a fourth end band 1309. In the tubular form, side bands 1301 and 1302 form a continuous helical winding for the central portion of the stent body while first and second end bands 1306 and 1307 form right cylinders to the longitudinal axis of the stent for the end rings of the stent. In the first end band, first edge 1350 is brought together with second edge 1351 while, in the second end band, first edge 1352 is brought together with second edge 1353. Main stent component 1300 comprises struts having one or more fenestrations into which a therapeutic substance may be deposited.

Each band is formed with struts of sufficient width to include one or more fenestrations as shown, for example, in FIG. 4. The fenestrated struts of main stent component 1300 may be of any geometric shape, including, but not limited to, round, oval or rectangular. Further, the fenestrations may extend through the entire thickness of the strut (full fenestrations), or may extend only partially through (partial fenestrations), being open only on one side of the strut (luminal or abluminal in the tubular form). Also, the stent may have struts containing fenestrations having variable sizes, numbers and shapes on one strut or between different struts. The invention contemplates struts having full and/or partial fenestrations on either or both of the side and/or end bands. The struts defining the peaks and troughs of the side bands may vary in length along the length of the main stent component to accommodate the desired shape for the resulting helically coiled stent structure and the number of fenestrations. For example, in FIG. 4A, side band struts 1358 and 1359 differ in length as do end band struts 1356 and 1357. The fenestrated struts are connected by loops or turns 1370 wherein the material is narrower than that of the fenestrated struts to provide enhanced flexibility.

Figures 5, 5A, 5B:
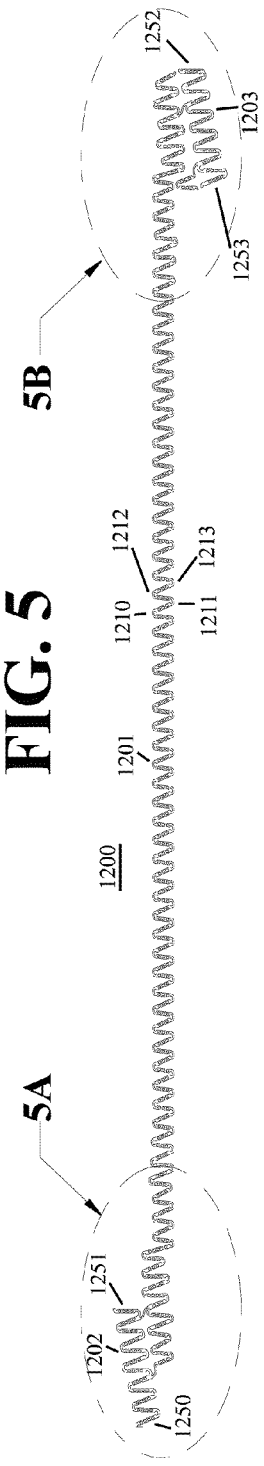
FIG. 5 illustrates a main stent component composed of a flat ribbon having undulations and comprising struts with one or more exemplary fenestrations.
FIG. 5A is an enlarged view of a first end band of the flat ribbon of FIG. 5.
FIG. 5B is an enlarged view of a second end band of the flat ribbon of FIG. 5.

FIG. 5 illustrates yet another embodiment of the invention where the main stent component 1200 is laid out in flat form, i.e., uncoiled. As depicted, the main stent component 1200 is a single side band 1201 in the longitudinal direction when laid flat. Side band 1201 is attached to first end band 1202 and second end band 1203 by cross-struts 1240 and 1241, respectively. Side band 1201 comprises an alternating pattern of peaks (e.g., 1210, 1212) and troughs (e.g., 1211, 1213) defined by struts having the same or variable lengths. Each side and end band is formed with struts having sufficient width to include one or more full or partial fenestrations, as described above for FIG. 4, and are also applicable to FIG. 5. The fenestrated struts are connected by loops or turns 1270 that are narrower than that of the fenestrated struts to provide enhanced flexibility. As shown in FIG. 5A, the struts are of varying length and vary in the number of fenestrations in each strut. For example, strut 1217 has a different length and number of fenestrations than strut 1215. Strut 1216 has a different length but the same number of fenestrations than strut 1215. And struts 1214 and 1215 have the same lengths and number of fenestrations. The stent of FIG. 5A contemplates that struts (e.g., 1217) near the ends of the first side band 1201 may have different lengths than struts 1214 and 1215 and are configured to aid in helical winding.

End bands 1202 and 1203 form circumferential end rings upon rolling of the structure into a stent. The first end band 1202 and second end band 1203 extend from the ends of the side band 1201 in a direction angularly offset from the general direction of the side band 1201. End bands 1202 and 1203 are configured to form right cylinders at the ends of the stent, flanking the helical windings of the central stent body upon winding of the structure into a stent. First end band 1202 has first edge 1250 and second edge 1251. In the tubular form, first edge 1250 is brought together with second edge 1251 to form a right cylinder to the longitudinal axis of the stent. Second end band 1203 has first edge 1252 and second edge 1253. In the tubular form, first edge 1252 is brought together with second edge 1253 to form a right cylinder to the longitudinal axis of the stent. As further explained below, the edges (1250 and 1251; 1252 and 1253) may be permanently affixed, or as an alternative, may be held in position with a securement which may keep the two edges in close proximity to maintain a right cylinder to the longitudinal axis of the stent.

In FIG. 5A, first end band 1202 comprises a band of undulations. The direction of the first end band 1202 is offset at an angle to the direction of the side band 1201. In FIG. 5A, the first end band extends from the side band is at an angle less than 45 degrees to the central body of the stent when the stent is laid flat. The undulating pattern of the first end band 1202 comprises alternating peaks (e.g., 1219, 1221) and troughs (e.g., 1220, 1222). Troughs (1220, 1222) of the first end band extend in the direction of the side band while the peaks (1219, 1221) point away from the side band. First end band 1202 also may contain struts having fenestrations. In FIG. 5A, cross-links 1240 and 1242, for example, connect the side band to the first end band. Cross-links 1240 and 1242 extend from the troughs of the first end band to the peak of the side band. Cross-links extending between the side band and the first end band are flexible connectors having one or more curved portions. The invention also contemplates an embodiment where the cross-links may contain one or more loops.

In FIG. 5B, second end band 1203 also comprises a band of undulations. The direction of the second end band 1203 is angularly offset to the direction of the side band 1201. Preferably, the second end band extends from the side band at an angle less than 45 degrees to the central body of the stent when the stent is laid flat. The undulating pattern of the second end band 1203 comprises alternating peaks (e.g., 1223, 1225) and troughs (e.g., 1224, 1226). Troughs (1224, 1226) of the second end band extend in the direction of the side band while the peaks (1223, 1225) point away from the side band. Second end band 1203 contains struts having fenestrations. In FIG. 5B, cross-link 1241 connects the side band to the second end band. Cross-link 1241 extends from the trough of the second end band to the trough of the side band. Cross-links extending between the side band and second end band are flexible connectors having one or more curved portions. Cross-links connecting the side band to the second end band may comprise at least one loop.

In addition, the invention contemplates other end bands similar in construction to first and second end bands and connected to either the first or second end bands to facilitate helical winding and uniform coverage. In FIG. 5B, a third end band 1204 having fenestrated struts is connected to the second end band by cross-link 1243. As illustrated in FIGS. 5A and 5B, the invention contemplates first and second end bands which are not identically connected to the undulating or patterned side bands and which are not identical to each other. Like the side band, any one or all the end bands may comprise struts sufficiently wide to accommodate one or more full or partial fenestrations which are connected together with loops having a narrower gauge than the fenestrated struts.

The main stent component may be held in a helically wound position by a second component, securing the helical windings into a tubular structure. The second component, referred to herein as a securement, may be one or more of a variety of means for securing the main stent component in the tubular form. The securement maintains the helical winding of the central stent body and/or the formation of right cylinders by the end bands. In one embodiment, the securement comprises a structure in the form of fibers, sheets, threads or ribbons which are wrapped around or itself embedded in the coiled main stent component. In another embodiment, wires or ribbons formed of a metal or non-metal material maintain the main stent component in its tubular configuration. The securement comprises a material that allows flexibility and expansion of the helical main stent component without tearing or detachment of the securement and allows movement between the coiled windings of the main stent body relative to each other. Such a material may be applied to a tubular stent in a continuous or non-continuous manner depending upon the particular needs of the structure contemplated.

Preferably, the securement allows expansion of the stent and maximal bending during and after implantation without reaching the elastic limit. The elastic range may be a product either of inherent elasticity in the material used, such as with certain polymers, or of the inclusion of a reserve length of a non-elastic material between points of connection with the main stent component. Yet another advantage of a securement is the prevention of "stent jail" phenomenon, or the complication of tracking into side branches covered by the stent. A further advantage is the high fatigue resistance of particular securement structures with high elastic range.

In one embodiment, the securement is a polymer that is a biocompatible material. Biocompatible material may be durable, such as polyesters, polyanhydrides, polyethylenes, polyorthoesters, polyphosphazenes, polyurethane, polycarbonate urethane, silicones, polyolefins, polyamides, polycaprolactams, polyimides, polyvinyl alcohols, acrylic polymers and copolymers, polyethers, celluiosics and any of their combinations in blends or as copolymers. Of particular use may be silicone backbone-modified polycarbonate urethane and/or expanded polytetrafluoroethylene (ePTFE). Any polymer having a high elastic ratio (high elongation factor within the elastic range) is particularly suitable for a securement. The polymer may also be porous. In embodiments where the polymer a continuous structure with small inter-fiber distance, it may also be used as a matrix for eluting drug thereby providing a uniform elution bed. This type of porous securement may be applied to any other stent structure.

Figure 6:
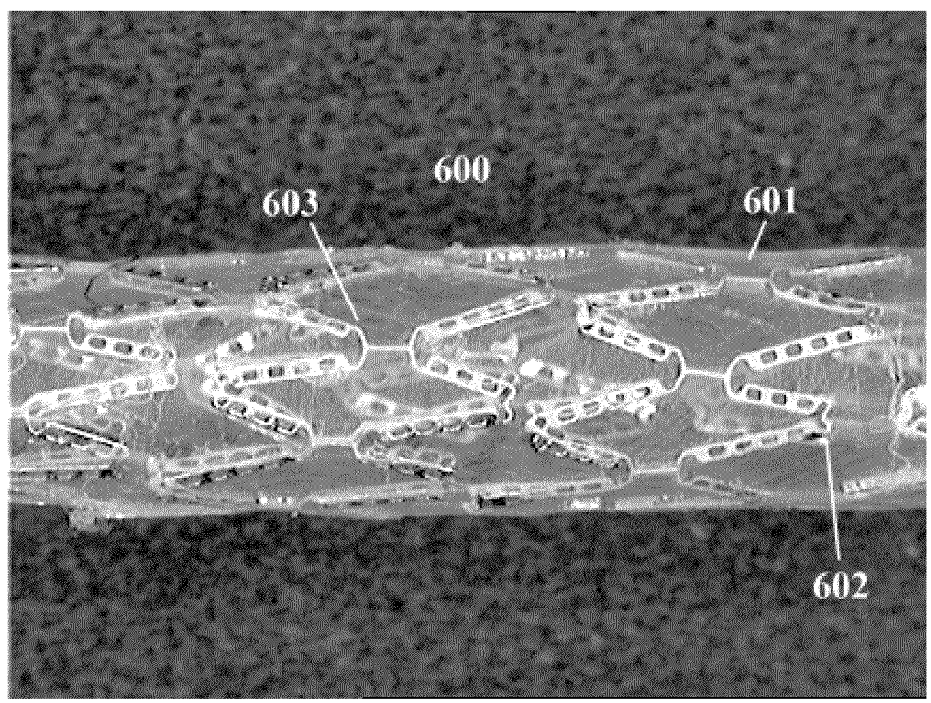
FIG. 6 illustrates a photograph of a securement structure and a main stent component.

FIG. 6 shows the coiled main stent component 600 of FIG. 4, described above, wherein a porous and durable polymer securement 601 is applied over main stent component 600. Two adjacent struts of a first side band are connected to one another by turn 602, which includes a "dimple". The inclusion of a dimple in the turns is an optional feature depending upon the desired properties of the resulting stent. FIG. 6 also illustrates turn 603 which is without a dimple, and is employed in this embodiment at points where cross-struts connect the first side band to the second side band.

Figure 7:
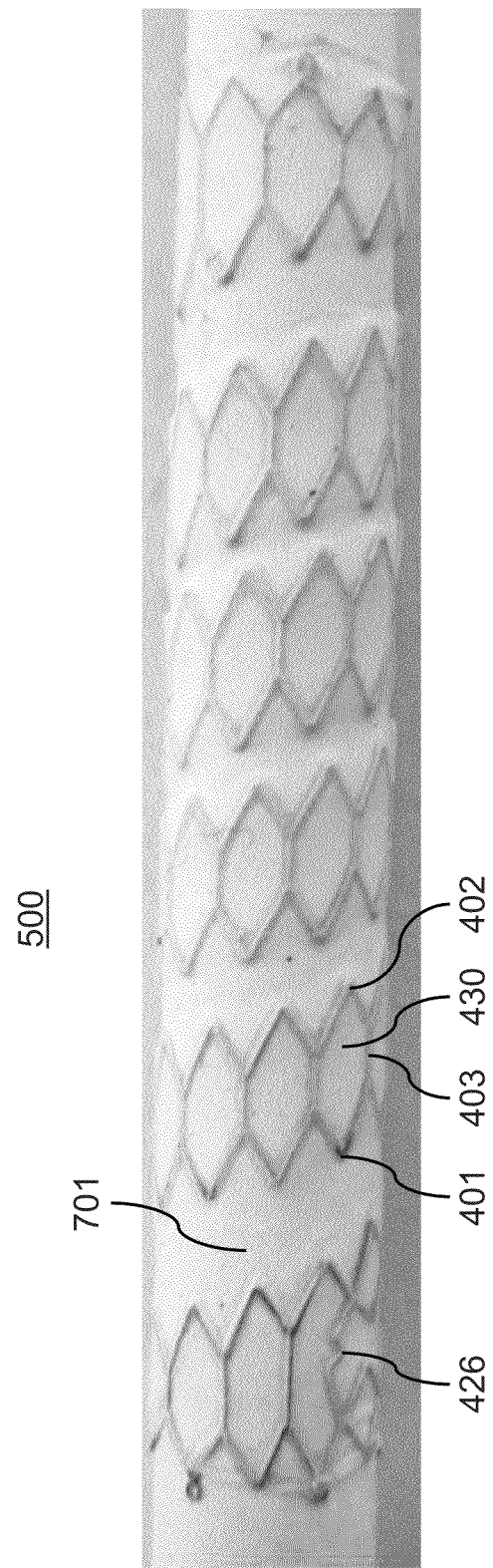
FIG. 7 illustrates an embodiment of a helical main stent component with a patterned band and embedded in a securement.

In FIG. 7, the helical main stent component 500 is secured by embedding the tubular structure in a polymer sheet 701 and illustrates one coiled form of the main stent component depicted in FIG. 2, that is, one where the adjacent helical coils of the stent are spaced apart but the stent maintains its helical structure through the embedded polymer securement. The securement may be disposed within interstices and/or embedded throughout the stent. In one embodiment, a polymer sheet may secure portions of the stent structure or may fully envelop the entire stent to hold the central portion in the helical form and the end bands in the cylindrical form.

Polymeric securements as described above may also be employed in the form of threads, wires or ribbons, thereby securing the main stent component through, for example, a series of points of connection with the main stent component. One or more securement threads, wires or ribbons may be coiled around the stent in a helically different direction than the main stent component. In particular, the thread, wire or ribbon may be coiled around the stent in the reverse helical orientation from the direction of the helically wound strip. Alternatively, securements may be arranged along a longitudinal axis of the stent. Arranged in any non-parallel direction with the main stent component, each thread, wire or ribbon may overlap with the main stent component in a regular pattern across the length of the stent and may effectively function to secure the helical stent body structure. The securement thread, wire or ribbon may be affixed to the main stent component at one or more points of overlap through a variety of means, e.g., welding, bonding, embedding, braiding, weaving, crimping, tying, press-fitting or the like, including also joining by adhesive means, e.g., gluing, dip coating, spray coating or the like. The polymeric securement may also be injected into a mold with or without the stent and hence become integrated within the stent. The threads, wires or ribbons maintain the tubular shape of the stent, while the longitudinally flexible quality of the polymeric material discussed above will enhance the overall flexibility of the stent.

Figure 8:
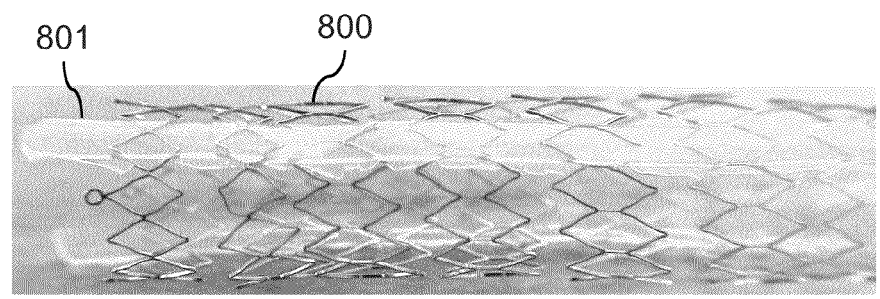
FIG. 8 illustrates an embodiment of the helical main stent component embedded in several ribbon securements.

FIG. 8 illustrates a helically coiled stent wherein the main stent component 800 forms a helically wound tubular structure that is secured in place by two ribbons 801. The ribbons 801 are a polymeric material that extend along the length of the stent. The ribbons may be affixed to the outside or the inside surface of the stent, or may be embedded in the helically coiled main stent component. In FIG. 8, the main stent component 800 is embedded within each ribbon 801 at points where the main stent component 800 and each second component ribbon 801 intersect.

Figure 9:
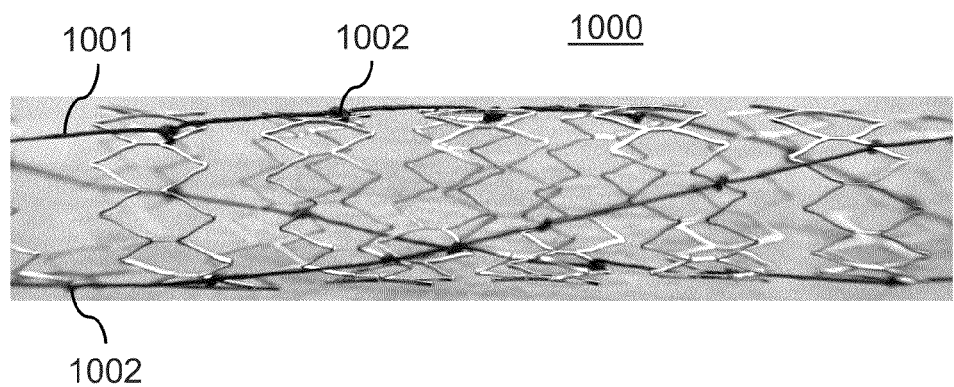
FIG. 9 illustrates a helical main stent component maintained by a plurality of helical securements fastened at discrete points.

FIG. 9 illustrate a helically coiled stent wherein the main stent component 1000 forms a tubular structure similar to FIG. 2 and one or more securement wires 1001 are coiled in a different helical direction to that of the coiled central body portion of the stent. The securement wires 1001 are affixed to the main stent component 1000 at various points of connection 1002 along the stent, thereby maintaining the helical, tubular structure.

In addition to polymeric securements, any other suitable material, including metals and/or non-metals, may be employed as securements in the form of threads, wires or ribbons to secure the main stent component. The metal or non-metal securement wire, thread or ribbon may be affixed to the main stent component where they overlap through one or more of a variety of means as identified above. If the material employed to manufacture the second component is of a lesser longitudinal flexibility than desired, increased flexibility may be achieved by increasing the length of the thread, wire or ribbon between points of connection, thereby providing reserve length of the second component that can extend upon expansion or bending of the stent.

In embodiments where the main stent component is an amorphous metal alloy, further advantages may be provided, i.e., enhanced corrosion resistance, resistance to unwanted permanent deformation and/or higher strength for a given metal thickness. Stents of the invention comprising amorphous metal alloys may also exhibit significantly lower conductance or are non-conductive, compared to their crystalline or polycrystalline counterparts. Such alloys may provide improved tensile strength, elastic deformation properties, and reduced corrosion potential to the devices. These may be important features in medical devices to provide an extended fatigue-resistant lifespan for devices that are subjected to repeated deformations and fatigue in the body. In addition, these features allow production of smaller or thinner devices that are as strong as their bulkier conventional counterparts.

In another embodiment, the amorphous metal alloy of the main stent component may be a metalloid, non-limiting examples of which include silicon, boron, and phosphorus. Another possible amorphous metal alloy is a Fe—Cr—B—P alloy. Many other similar alloys are suitable and known to one of ordinary skill in the art. One embodiment of this invention contemplates intraluminal prosthetic devices comprising at least one amorphous metal alloy combined with components made of other materials, limited only by the biocompatibility of the materials. This embodiment of the invention may contain one or more amorphous metal alloys. For example, the device may have components constructed of stainless steel, cobalt chromium ("CoCr"), NiTi or other known materials. The details of these alloys, which have certain advantages, are disclosed in U.S. Pat. Nos. 5,836,964 and 5,997,703, which are hereby expressly incorporated by reference.

The methods of manufacturing the amorphous metal alloys are described in U.S. application Ser. No. 12/428,347, filed on Apr. 22, 2009, the contents of which are hereby incorporated by reference. Amorphous metal stents of the invention may be formed of one or more flat strips of helically wound metal. Because amorphous metal alloys cannot be easily welded without the metal reverting to an undesirable crystalline form, the present invention contemplates a securement for the helically wound amorphous metal alloy main stent component, further described below.

Where the main stent component is an amorphous metal alloy, the method of combining or joining the amorphous metal alloy to the securements can be achieved using particular methods known in the art. For example, a biocompatible polymer securement covering all or part of the amorphous metal main stent component may be used to secure the helical windings in its tubular shape for positioning and expansion in the lumen as well as the end bands in a cylindrical shape. Other non-limiting examples of securement methods include physical joining (e.g., braiding, weaving, crimping, tying, and press-fitting) and joining by adhesive methods (e.g., gluing, dip coating, and spray coating). Combinations of these methods are also contemplated by this invention.

As a further advantage of the invention, any or all of the securement or main stent component may be embedded with a therapeutic agent that will inhibit or decrease cell proliferation or will reduce restenosis. The main stent component may comprise at least one fenestration where the drug is deposited. Non-limiting examples of such drugs include for example sirolimus, rapamycin, everolimus and paclitaxol, and analogs of these. In addition, the stent may be treated to have active or passive surface components such as agents that will be advantageous for a longer time after the stent is embedded in the vessel wall.

The stent of the present invention may be balloon expandable or self-expanding as is known in the art. When a balloon-expandable stent system is used to deliver the stent, the stent is mounted on the balloon and the catheter assembly is positioned at the implantation site. The balloon is then inflated, radially applying a force inside the stent and the stent is expanded to its expanded diameter. Alternatively, the stent may be self-expanding in which case a balloon is not needed to facilitate expansion and delivery of the stent.

The general concepts described herein can be utilized to form helical stents with different configurations than the particular embodiments described herein. It will be appreciated by persons skilled in the art that the present invention is not limited to what has been particularly shown and described above. Rather, the scope of the present invention is defined by the claims which follow.

The invention claimed is:

1. A stent having a tubular structure comprising:
a helically coiled main stent component having a first side band and a second side band, the first and second side bands being helically wound a plurality of times to form a plurality of windings, a first end band connected to said first side band and extending at an oblique angle from said first side band, and a second end band connected to said second side band and extending at an oblique angle from said second side band, wherein each of the bands has an undulating pattern, wherein the first and second side bands are each helically oriented and intermittently connected, and the first and second end bands each form a right cylinder at the longitudinal ends of the stent; and
a securement interconnecting the windings of the main stent component.

2. The main stent component of claim 1 wherein one or more said side bands contain struts having one or more fenestrations.

3. The main stent component of claim 2 wherein said fenestration is filled with a therapeutic agent.

4. The stent according of claim 1 wherein said first side band is nestled next to a helically neighboring second side band.

5. The main stent component of claim 1 wherein the first and second side bands are connected by at least one cross strut.

6. The main stent component according to claim 5, wherein at least one said cross strut has a loop.

7. The securement of claim 1 wherein said securement comprises a structure selected from a group consisting of a sheet, a thread, a wire and a ribbon.

8. The securement of claim 7, wherein said securement is wound around the stent in a helical path different from the helical path of the main stent component.

9. The securement of claim 7, wherein the securement overlaps at a point of connection with the main stent component periodically over the length of the stent.

10. The securement of claim 1 comprising a fiber mesh.

11. The securement of claim 1 comprising a porous material.

12. The securement of claims 1 comprising a durable material.

13. The securement of claim 12 wherein the durable material is polyurethane.

14. The securement of claim 1, wherein said securement is embedded across the entire length of the helical main stent component.

15. The securement of claim 1, wherein the securement is affixed to the helical main stent component at an end.

16. A cylindrical main stent component comprising a strip comprising:
a first side band having undulations;
a second side band having undulations and connected to the first side band, wherein said first side band and second side band are helically oriented and are helically wound a plurality of times to form a plurality of windings; and
a first end band having undulations, a first edge, and a second edge, said first end band connected to said first side band and extending at an oblique angle to said first side band.

17. The strip main stent component of claim 16 further comprising: a second end band having undulations, a first edge and a second edge, said second end band connected to said second side band and extending at an oblique angle to said second side band.

18. The strip main stent component of claim 16, wherein said side band and end band having an undulating pattern of struts joined by loops, wherein one or more said struts contain a fenestration and said loops having a width narrower than the width of said struts containing said fenestration.

19. The strip main stent component of claim 18 wherein said fenestration is filled with a therapeutic agent.

20. The main stent component of claim 18, wherein some adjacent struts of the undulating pattern have the same lengths.

21. The main stent component of claim 16 wherein the first and second side bands are connected by at least one cross strut.

22. The main stent component according to claim 21, wherein at least one said cross strut has a loop.

23. The main stent component of claim 16 comprising a metal.

24. The main stent component of claim 16 cut from a flat sheet of metal.

25. The main stent component of claim 16 comprising an amorphous metal alloy.

26. The main stent component of claim 25, wherein said amorphous metal alloy comprises an element selected from the group consisting of silicon, boron, and phosphorous.

27. The main stent component according to claim 25, wherein said amorphous metal alloy is an iron-based alloy containing Fe, Cr, B, and P.

28. The main stent component according to claim 25 wherein the amorphous metal alloy contains silicon.

29. The main stent component according to claim 25 wherein the amorphous metal alloy comprises a Fe—Cr—B—P alloy.

30. A cylindrical main stent component comprising:
a helically oriented side band having undulations, said side band being helically wound a plurality of times to form a plurality of windings;
a first end band having undulations, a first edge and a second edge, said first end band connected to said side band and extending at an oblique angle to said side band; and
a second end band having undulations, a first edge and a second edge, said second end band connected to said side band and extending at an oblique angle to said side band, wherein said side band and end band having an undulating pattern of struts joined by loops, wherein one or more said struts contain a fenestration and said loops having a width narrower than the width of said struts containing said fenestration.

31. The main stent component according to claim 30 wherein said fenestration is filled with a therapeutic agent.

32. The main stent component of claim 30, wherein some adjacent struts of the undulating pattern have the same lengths.

33. The main stent component of claim 30 comprising a metal.

34. The main stent component of claim 30 cut from a flat sheet of metal.

35. The main stent component of claim 30 comprising an amorphous metal alloy.

36. The main stent component of claim 35, wherein said amorphous metal alloy comprises an element selected from the group consisting of silicon, boron, and phosphorous.

37. The main stent component according to claim 35, wherein said amorphous metal 20 alloy is an iron-based alloy containing Fe, Cr, B, and P.

38. The main stent component according to claim 35 wherein the amorphous metal alloy contains silicon.

39. The main stent component according to claim 35 wherein the amorphous metal alloy comprises a Fe—Cr—B—P alloy.

40. A method of making a stent from the flat strip of claim 16, comprising the steps of:
a) helically winding the main stent component along a longitudinal axis; and
b) bringing the first edge of the first end band with the second edge of the first end band in close proximity to form a right cylinder to the longitudinal axis of the stent.

41. The method of claim 40, further comprising the step of applying a securement.

42. A method of making a stent from the main stent component of claim 30, comprising the steps of:
a) helically winding the main stent component along a longitudinal axis to form a helically coiled structure;
b) bringing the first edge of the first end band with the second edge and the first end band into close proximity to form a right cylinder to the longitudinal axis; and
c) bringing the first edge of the second end band with the second edge of the second end band into close proximity to form a right cylinder to the longitudinal axis.

43. The method of any of claim 42, further comprising the step of applying a securement.

44. The main stent component according to claim 30 wherein the side band is a first side band, said main stent component further comprising a second side band having an undulating pattern.

45. The main stent component according to claim 44, wherein the first and second side bands are intermittently connected.

46. The main stent component of claim 45 wherein the first and second side bands are connected by at least one cross strut.

47. The main stent component according to claim 46, wherein at least one said cross strut has a loop.

48. The main stent component according to claim 44 wherein the second side contains struts having one or more fenestrations.

49. The main stent component of claim 48 wherein said fenestration is filled with a therapeutic agent.

50. The main stent component according of claim 44 configured such that said first side band is nestled next to a helically neighboring second side band upon arrangement in a tubular structure.

51. The main stent component according to claim 44 wherein the main stent component is arranged in a tubular structure.

52. The main stent component according to claim 51 having a securement maintaining the tubular structure of the main stent component.

53. The main stent component of claim 52 wherein said securement comprises a structure selected from a group consisting of a sheet, a thread, a wire and a ribbon.

54. The main stent component of claim 53, wherein said securement is wound around the stent in a helical path different from the helical path of the main stent component.

55. The main stent component of claim 53, wherein the securement overlaps at a point of connection with the main stent component periodically over the length of the stent.

56. The main stent component of claim 52, wherein said securement comprises a fiber mesh.

57. The main stent component of claim 52, wherein said securement comprises a porous material.

58. The main stent component of claims 52, wherein said securement comprises a durable material.

59. The main stent component of claim 58 wherein the durable material is polyurethane.

60. The main stent component of claim 52, wherein said securement is embedded across the entire length of the helical main stent component.

61. The main stent component of claim 52, wherein the securement is affixed to the helical main stent component at an end.

62. The main stent component of claim 52, wherein the securement provides longitudinal flexibility for the stent.

63. The main stent component of claim 52, wherein the securement provides structural support for the stent.

64. The main stent component of claim 52, wherein the main stent component forms a plurality of windings along the longitudinal axis of the stent, and the securement interconnects adjacent windings of the main stent component in the longitudinal direction.

65. The method of claim 40, further comprising the step of applying a polymer to the main stent component by electrospinning.

66. The method of claim 42, further comprising the step of applying a polymer to the main stent component by electrospinning.

* * * * *